US009709568B2

(12) United States Patent
Pierce et al.

(10) Patent No.: US 9,709,568 B2
(45) Date of Patent: Jul. 18, 2017

(54) ANTIBODIES THAT BIND TO HUMAN PROGRAMMED DEATH LIGAND 1 (PD-L1)

(71) Applicant: Merck Sharp & Dohme Corp., Rahway, NJ (US)

(72) Inventors: Robert H. Pierce, La Jolla, CA (US); Patricia Bourne, Palo Alto, CA (US); Linda Liang, Mountain View, CA (US); Michael Bigler, Palo Alto, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/653,868

(22) PCT Filed: Dec. 18, 2013

(86) PCT No.: PCT/US2013/075932
§ 371 (c)(1),
(2) Date: Jun. 19, 2015

(87) PCT Pub. No.: WO2014/100079
PCT Pub. Date: Jun. 26, 2014

(65) Prior Publication Data
US 2015/0355184 A1 Dec. 10, 2015

Related U.S. Application Data

(60) Provisional application No. 61/745,386, filed on Dec. 21, 2012.

(51) Int. Cl.
*G01N 33/574* (2006.01)
*G01N 33/68* (2006.01)
*C07K 16/28* (2006.01)

(52) U.S. Cl.
CPC ... *G01N 33/57492* (2013.01); *C07K 16/2827* (2013.01); *G01N 33/57407* (2013.01); *G01N 33/6872* (2013.01); *G01N 33/6878* (2013.01); *C07K 2317/31* (2013.01); *C07K 2317/34* (2013.01); *C07K 2317/565* (2013.01); *G01N 2333/70532* (2013.01)

(58) Field of Classification Search
CPC ............ C07K 2317/30; C07K 2317/24; C07K 2317/56; C07K 2317/565
USPC .......................... 424/133.1, 172.1; 530/387.9
See application file for complete search history.

(56) References Cited

FOREIGN PATENT DOCUMENTS

WO    WO 2013/173223    11/2013

OTHER PUBLICATIONS

NCBI Protein database ("human PD-L1"; p. 1; Sep. 8, 2016).*
George et al. (Circulation. 1998; 97: 900-906).*
Bigelow, Elaine et al; "Immunohistochemical staining of B7-H1 (PD-L1) on paraffin-embedded slides of pancreatic adenocarcinoma tissue", XP002722587, Database accession No. NLM23328703 abstract; Database Medline [Online] US National Library of Medicine (NLM), Bethesda, MD, US; 2013.
Bigelow, Elaine et al: "Immunohistochemical staining of B7-H1 (PD-L1) on paraffin-embedded slides of pancreatic adenocarcinoma tissue", Journal of visualized experiments : JoVE,Mar. 1, 2013 (Mar. 1, 2013), XP055111169, Retrieved from the Internet: URL:http://www.jove.com/video/4059/immunoh istochemical-staining-b7-hl-pd-II-on-paraf fin-embedded slides [retrieved on Apr. 1, 2014] the whole document.
Chen, Benjamin J et al; "PD-L1 Expression Is Characteristic of a Subset of Aggressive B-cell Lymphomas and Virus-Associated Malignancies" , Clinical Cancer Research, The American Association for Cancer Research, US, vol. 19, No. 13, Jul. 1, 2013 (Jul. 1, 2013), pp. 3462-3473.
Ding, H et al; "PD-L1 is expressed by human renal tubular epithelial cells and suppresses T cell cytokine synthesis", Clinical Immunology, Academic Press, US, vol. 115, No. 2, May 1, 2005 (May 1, 2005), pp. 184-191.
Gadiot, Jules et al:"Overall survival and PD-L1 expression in metastasized malignant melanoma"; Cancer; vol. 117 No. 10; Nov. 29, 2010 (Nov. 29, 2010) pp. 2192-2201.
Hamanishi, J. et al; "Programmed cel 1 death 1 ligand 1 and tumor-infiltrating CD8+ T lymphocytes are prognostic factors of human ovarian cancer", Proceedings of the National Academy of Sciences, vol. 104, No. 9, Feb. 27, 2007 (Feb. 27, 2007), pp. 3360-3365.
Li, Hong et al; "The characteristic expression of B7-associated proteins in Langerhans cell sarcoma", ACTA Histochemica, Elsevier, Amsterdam, NL, vol. 114, No. 7, Dec. 21, 2011 (Dec. 21, 2011), pp. 733-743.
Hua, Dong; "B7-H1 expression is associated with expansion of regulatory T cells in colorectal carcinoma"; World Journal of Gastroenterology, vol. 18, No. 9, Jan. 1, 2012 (Jan. 1, 2012), p. 971.
International Search Report, International Application No. PCT/US2008/007463, Date of Mailing Oct. 29, 2008.
Kronig, Holger et al; "PD-1 expression on Melan-A-reactive T cells increases during progression to metastatic disease"; International Journal of Cancer, vol. 130, No. 10, Jan. 11, 2012 (Jan. 11, 2012), pp. 2327-2336.

(Continued)

*Primary Examiner* — Lynn Bristol
(74) *Attorney, Agent, or Firm* — Alysia A. Finnegan; Gloria M. Fuentes

(57) ABSTRACT

The present disclosure provides isolated antibodies that specifically bind to human PD-L1, as well as antigen binding fragments of such antibodies, and kits comprising the anti-PD-L1 antibodies or binding fragments and a set of reagents for detecting a complex of the antibody, or antigen binding fragment thereof, bound to human PD-L1. The antibodies and antigen binding fragments of this disclosure are useful for immunohistochemical detection of human PD-L1 expression in tissue samples. Nucleic acid molecules encoding the antibodies and antigen binding fragments of this disclosure, as well as expression vectors and host cells for expression thereof, are also provided.

8 Claims, 13 Drawing Sheets

(56) References Cited

OTHER PUBLICATIONS

Wang, Liancai et al; "Clinical Significance of B7-H1 and B7-1 Expressions in Pancreatic Carcinoma", World Journal of Surgery ; Official Journal of the Internationalsociety of Surgery/Societe Internationale De Chirurgie, Springer-Verlag, NE, vol. 34, No. 5, Feb. 10, 2010 (Feb. 10, 2010), pp. 1059-1065.
Shi, Sheng-Jia et al; "B7-H1 Expression Is Associated with Poor Prognosis in Colorectal Carcinoma and Regulates the Proliferation and Invasion of HCT116 Colorectal Cancer Cells", PLOS ONE, vol. 8, No. 10, Oct. 4, 2013 (Oct. 4, 2013), p. e76012.
Thompson, R H et al; "Tumor B7-H1 is associated with poor prognosis in renal cell carcinoma patients with long-term follow-up", Cancer Research, American Association for Cancer Research, US, vol. 66, No. 7, Apr. 1, 2006 (Apr. 1, 2006), pp. 3381-3385.
Wu, C. et al; "Immunohistochemical localization of programmed death-I ligand-1 (PD-L1) in gastric carcinoma and its clinical significance", ACTA Histochemica, Elsevier, Amsterdam, NL, vol. 108, No. 1, May 10, 2006 (May 10, 2006), pp. 19-24.
Written Opinion, International Application No. PCT/ US2008/007463, Date of Mailing Dec. 18, 2009.
International Search Report of PCT/US2008/007463, mailed Oct. 29, 2008.
Written Opinion of PCT/US2008/007463, mailed Dec. 18, 2009.
International Search Report of PCT/US2013/075932 mailed May 22, 2014.
Written Opinion of PCT/US2013/075932 mailed May 22, 2014.

\* cited by examiner

Antibody 20C3

Heavy chain

[ATGGAAAGGCACTGGATCTTTCTCTTCCTGTTTTCAGTAACTGCAGGTGTCCACTCC]

CAGGTCCAGGTTCAGCAGTCTGGGGCTGAACTGGCAGAACCTGGGGCCTCAGTGAAGATGTCCTGCAAGGCCTC
TGGCTACATCTTTACTAGCTACTGGATGCACTGGCTAAAGCAGAGGCCTGGACAGGGTCTGGAATGGATTGGAT
ACATTAATCCCAGCAGTGATTATAATGAATACAGTGAGAAATTCATGGACAAGGCCACATTGACTGCAGACAAA
GCCTCCACCACAGCCTACATGCAACTGATCAGCCTGACATCTGAGGACTCTGCAGTCTATTACTGTGCAAGATC
GGGATGGTTAGTACATGGAGACTATTATTTTGACTACTGGGGCCAAGGCACCACTCTCACAGTCTCCTCA

[MERHWIFLFLFSVTAGVHS]
QVQVQQSGAELAEPGASVKMSCKASGYIFT<u>SYWMH</u>WLKQRPGQGLEWIG<u>YINPSSDYNEYSEKFMD</u>KATLTADK
ASTTAYMQLISLTSEDSAVYYCAR<u>SGWLVHGDYYFDY</u>WGQGTTLTVSS

Light chain

[ATGGATTCACAGGCCCAGGTTCTTATATTGCTGCTGCTATGGGTATCTGGTACCTTTGGG]

GACATTGTGATGTCACAATCTCCATCCTCCCTGGCTGTGTCAGCAGGAGAGAAGGTCACTATGAGCTGCAAATC
CAGTCAGAGTCTGCTCAACAGTAGAACCCGAAAGAACTACTTGGCTTGGTACCAGCAGAAACCAGGGCAGTCTC
CTAAACTGCTGATCTACTGGGCATCCACTAGGGAATCTGGGGTCCCTGATCGCTTCACAGGCAGTGGATCTGGG
ACAGATTTCACTCTCACCATCAGCAGTGTGCAGGCTGAAGACCTGGCAGTTTATTACTGCCAGCAATCTTATGA
TGTGGTCACGTTCGGTGCTGGGACCAAGCTGGAGCTGAAA

[MDSQAQVLILLLLWVSGTFG]
DIVMSQSPSSLAVSAGEKVTMSC<u>KSSQSLLNSRTRKNYLA</u>WYQQKPGQSPKLLIY<u>WASTRES</u>GVPDRFTGSGSG
TDFTLTISSVQAEDLAVYYC<u>QQSYDVVT</u>FGAGTKLELK

FIG. 1

Antibody 22C3

Heavy chain

[ATGGAAAGGCACTGGATCTTTCTCTTCCTGTTTTCAGTAACTGCAGGTGTCCACTCC]

CAGGTCCACCTTCAGCAGTCTGGGGCTGAACTGGCAAAACCTGGGGCCTCAGTGAAGATGTCCTGCAAGGCTTC
TGGCTACACGTTTACTAGTTACTGGATACACTGGATAAAGCAGAGGCCTGGACAGGGTCTGGAATGGATTGGAT
ACATTAATCCTTCCTCTGGTTATCATGAATACAATCAGAAATTCATTGACAAGGCCACATTGACTGCTGACAGA
TCCTCCAGCACAGCCTACATGCACCTGACCAGCCTGACGTCTGAAGACTCTGCAGTCTATTACTGTGCAAGATC
GGGATGGTTAATACATGGAGACTACTACTTTGACTTCTGGGGCCAAGGCACCACTCTCACAGTCTCCTCA

[MERHWIFLFLFSVTAGVHS]
QVHLQQSGAELAKPGASVKMSCKASGYTFT<u>SYWIH</u>WIKQRPGQGLEWIG<u>YINPSSGYHEYNQKFID</u>KATLTADR
SSSTAYMHLTSLTSEDSAVYYCAR<u>SGWLIHGDYYFDF</u>WGQGTTLTVSS

Light chain

[ATGGATTCACAGGCCCAGGTTCTTATATTGCTGCTGCTATGGGTATCTGGTACCTGTGGG]

GACATTGTGATGTCACAGTCTCCCTCCTCCCTGGCTGTGTCAGCAGGAGAGAAGGTCACTATGACCTGCAAATC
CAGTCAGAGTCTGCTCCACACTAGCACCCGAAAGAACTACTTGGCTTGGTACCAGCAGAAACCAGGGCAGTCTC
CTAAACTGCTGATCTATTGGGCATCCACTAGGGAATCTGGGGTCCCTGATCGCTTCACAGGCAGTGGATCTGGG
ACAGATTTCACTCTCACCATCAGCAGTGTGCAGGCTGAAGACCTGGCAGTTTATTACTGCAAACAATCTTATGA
TGTGGTCACGTTCGGTGCTGGGACCAAGCTGGAGCTGAAA

[MDSQAQVLILLLLWVSGTCG]
DIVMSQSPSSLAVSAGEKVTMTC<u>KSSQSLLHTSTRKNYLA</u>WYQQKPGQSPKLLIY<u>WASTRES</u>GVPDRFTGSGSG
TDFTLTISSVQAEDLAVYYC<u>KQSYDVVT</u>FGAGTKLELK

FIG.2

Alignment of Mature Variable Regions

Light Chain

20C3 DIVMSQSPSSLAVSAGEKVTMSC<u>KSSQSLLNSRTRKNYLA</u>WY
22C3 DIVMSQSPSSLAVSAGEKVTMTC<u>KSSQSLLHTSTRKNYLA</u>WY
                                CDR1

20C3 QQKPGQSPKLLIY<u>WASTRES</u>GVPDRFTGSGSGTDFTLTISSV
22C3 QQKPGQSPKLLIY<u>WASTRES</u>GVPDRFTGSGSGTDFTLTISSV
                   CDR2

20C3 QAEDLAVYYC<u>QQSYDVVT</u>FGAGTKLELK
22C3 QAEDLAVYYC<u>KQSYDVVT</u>FGAGTKLELK
              CDR3

Heavy Chain

20C3 QVQVQQSGAELAEPGASVKMSCKASGEYIFT<u>SYWMH</u>WLKQRPGQGL
22C3 QVHLQQSGAELAKPGASVKMSCKASGEYTFT<u>SYWIH</u>WIKQRPGQGL
                                     CDR1

20C3 EWIGY<u>INPSSDYNEYSEKFMD</u>KATLTADKASTTAYMQLISLTSED
22C3 EWIGY<u>INPSSGYHEYNQKFID</u>KATLTADRSSSTAYMHLTSLTSED
           CDR2

20C3 SAVYYCAR<u>SGWLVHGDYYFDY</u>WGQGTTLTVSS
22C3 SAVYYCAR<u>SGWLIHGDYYFDF</u>WGQGTTLTVSS
             CDR3

FIG.3

Engineered Controls
CHO parental (negative control)  hPD-L1 transfected CHO (positive control)
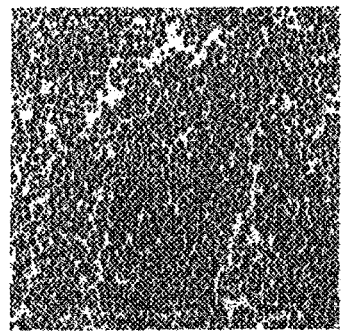 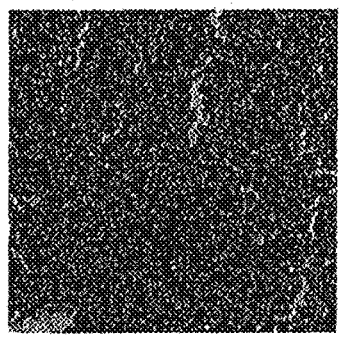
FIG.7A
Human Cell Lines
A375  HS578T  LOX
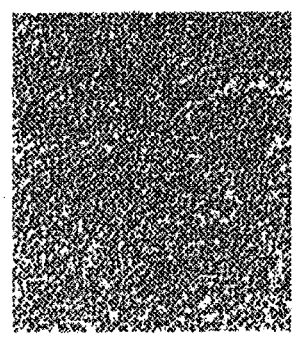 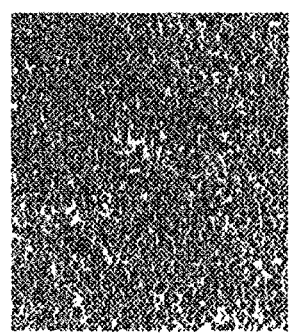 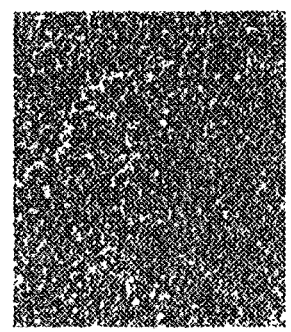
PD-L1 mRNA
(qPCR, relative    21         8         128
to ubiquitin)
FIG.7B

SEQUENCE LISTING

<160> NUMBER OF SEQ ID NOS: 36

<210> SEQ ID NO 1
<211> LENGTH: 17
<212> TYPE: PRT
<213> ORGANISM: Artificial Sequence

```
<220> FEATURE:
<223> OTHER INFORMATION: Consensus Sequence
<220> FEATURE:
<221> NAME/KEY: MISC_FEATURE
<222> LOCATION: (8)..(8)
<223> OTHER INFORMATION: Xaa at position 8 may be His or Asn
<220> FEATURE:
<221> NAME/KEY: MISC_FEATURE
<222> LOCATION: (9)..(9)
<223> OTHER INFORMATION: Xaa at position 9 may be Ser or Thr
<220> FEATURE:
<221> NAME/KEY: MISC_FEATURE
<222> LOCATION: (10)..(10)
<223> OTHER INFORMATION: Xaa at position 10 may be Arg or Ser

<400> SEQUENCE: 1

Lys Ser Ser Gln Ser Leu Leu Xaa Xaa Xaa Thr Arg Lys Asn Tyr Leu
1               5                   10                  15

Ala

<210> SEQ ID NO 2
<211> LENGTH: 7
<212> TYPE: PRT
<213> ORGANISM: Mus musculus

<400> SEQUENCE: 2

Trp Ala Ser Thr Arg Glu Ser
1               5

<210> SEQ ID NO 3
<211> LENGTH: 8
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (1)..(1)
<223> OTHER INFORMATION: Xaa at position 1 may be Gln or Lys

<400> SEQUENCE: 3

Xaa Gln Ser Tyr Asp Val Val Thr
1               5

<210> SEQ ID NO 4
<211> LENGTH: 112
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (22)..(22)
<223> OTHER INFORMATION: Xaa at position 22 may be Ser or Thr
<220> FEATURE:
<221> NAME/KEY: MISC_FEATURE
<222> LOCATION: (31)..(31)
<223> OTHER INFORMATION: Xaa at position 31 may be His or Asn
<220> FEATURE:
<221> NAME/KEY: MISC_FEATURE
<222> LOCATION: (32)..(32)
<223> OTHER INFORMATION: Xaa at position 32 may be Ser or Thr
<220> FEATURE:
<221> NAME/KEY: MISC_FEATURE
<222> LOCATION: (33)..(33)
<223> OTHER INFORMATION: Xaa at position 33 may be Arg or Ser
<220> FEATURE:
<221> NAME/KEY: MISC_FEATURE
<222> LOCATION: (95)..(95)
<223> OTHER INFORMATION: Xaa at position 95 may be Gln or Lys

<400> SEQUENCE: 4
```

-continued

```
Asp Ile Val Met Ser Gln Ser Pro Ser Ser Leu Ala Val Ser Ala Gly
1               5                   10                  15

Glu Lys Val Thr Met Xaa Cys Lys Ser Ser Gln Ser Leu Leu Xaa Xaa
            20                  25                  30

Xaa Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Xaa Gln
                85                  90                  95

Ser Tyr Asp Val Val Thr Phe Gly Ala Gly Thr Lys Leu Glu Leu Lys
            100                 105                 110
```

<210> SEQ ID NO 5
<211> LENGTH: 5
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (4)..(4)
<223> OTHER INFORMATION: Xaa at position 4 may be Ile or Met

<400> SEQUENCE: 5

```
Ser Tyr Trp Xaa His
1               5
```

<210> SEQ ID NO 6
<211> LENGTH: 17
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (7)..(7)
<223> OTHER INFORMATION: Xaa at position 7 may be Asp or Gly
<220> FEATURE:
<221> NAME/KEY: MISC_FEATURE
<222> LOCATION: (9)..(9)
<223> OTHER INFORMATION: Xaa at position 9 may be His or Asn
<220> FEATURE:
<221> NAME/KEY: MISC_FEATURE
<222> LOCATION: (12)..(12)
<223> OTHER INFORMATION: Xaa at position 12 may be Ser or Asn
<220> FEATURE:
<221> NAME/KEY: MISC_FEATURE
<222> LOCATION: (13)..(13)
<223> OTHER INFORMATION: Xaa at position 13 may be Glu or Gln
<220> FEATURE:
<221> NAME/KEY: MISC_FEATURE
<222> LOCATION: (16)..(16)
<223> OTHER INFORMATION: Xaa at position 16 may be Ile or Met

<400> SEQUENCE: 6

```
Tyr Ile Asn Pro Ser Ser Xaa Tyr Xaa Glu Tyr Xaa Xaa Lys Phe Xaa
1               5                   10                  15

Asp
```

<210> SEQ ID NO 7
<211> LENGTH: 13
<212> TYPE: PRT
<213> ORGANISM: Artificial Sequence -continued

```
<220> FEATURE:
<223> OTHER INFORMATION: Consensus Sequence
<220> FEATURE:
<221> NAME/KEY: MISC_FEATURE
<222> LOCATION: (5)..(5)
<223> OTHER INFORMATION: Xaa at position 5 may be Ile or Val
<220> FEATURE:
<221> NAME/KEY: MISC_FEATURE
<222> LOCATION: (13)..(13)
<223> OTHER INFORMATION: Xaa at position 13 may be Phe or Tyr

<400> SEQUENCE: 7

Ser Gly Trp Leu Xaa His Gly Asp Tyr Tyr Phe Asp Xaa
1               5                   10

<210> SEQ ID NO 8
<211> LENGTH: 122
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (3)..(3)
<223> OTHER INFORMATION: Xaa at position 3 may be His or Gln
<220> FEATURE:
<221> NAME/KEY: MISC_FEATURE
<222> LOCATION: (4)..(4)
<223> OTHER INFORMATION: Xaa at position 4 may be Leu or Val
<220> FEATURE:
<221> NAME/KEY: MISC_FEATURE
<222> LOCATION: (13)..(13)
<223> OTHER INFORMATION: Xaa at position 13 may be Glu or Lys
<220> FEATURE:
<221> NAME/KEY: MISC_FEATURE
<222> LOCATION: (34)..(34)
<223> OTHER INFORMATION: Xaa at position 34 may be Ile or Met
<220> FEATURE:
<221> NAME/KEY: MISC_FEATURE
<222> LOCATION: (37)..(37)
<223> OTHER INFORMATION: Xaa at position 37 may be Ile or Leu
<220> FEATURE:
<221> NAME/KEY: MISC_FEATURE
<222> LOCATION: (56)..(56)
<223> OTHER INFORMATION: Xaa at position 56 may be Asp or Gly
<220> FEATURE:
<221> NAME/KEY: MISC_FEATURE
<222> LOCATION: (58)..(58)
<223> OTHER INFORMATION: Xaa at position 58 may be His or Asn
<220> FEATURE:
<221> NAME/KEY: MISC_FEATURE
<222> LOCATION: (61)..(61)
<223> OTHER INFORMATION: Xaa at position 61 may be Asn or Ser
<220> FEATURE:
<221> NAME/KEY: MISC_FEATURE
<222> LOCATION: (62)..(62)
<223> OTHER INFORMATION: Xaa at position 62 may be Glu or Gln
<220> FEATURE:
<221> NAME/KEY: MISC_FEATURE
<222> LOCATION: (65)..(65)
<223> OTHER INFORMATION: Xaa at position 65 may be Ile or Met
<220> FEATURE:
<221> NAME/KEY: MISC_FEATURE
<222> LOCATION: (74)..(74)
<223> OTHER INFORMATION: Xaa at position 74 may be Lys or Arg
<220> FEATURE:
<221> NAME/KEY: MISC_FEATURE
<222> LOCATION: (75)..(75)
<223> OTHER INFORMATION: Xaa at position 75 may be Ala or Ser
<220> FEATURE:
<221> NAME/KEY: MISC_FEATURE
<222> LOCATION: (77)..(77)
<223> OTHER INFORMATION: Xaa at position 77 may be Ser or Thr
<220> FEATURE:
<221> NAME/KEY: MISC_FEATURE
<222> LOCATION: (82)..(82)
<223> OTHER INFORMATION: Xaa at position 82 may be His or Gln
```

```
<220> FEATURE:
<221> NAME/KEY: MISC_FEATURE
<222> LOCATION: (84)..(84)
<223> OTHER INFORMATION: Xaa at position 84 may be Ile or Thr
<220> FEATURE:
<221> NAME/KEY: MISC_FEATURE
<222> LOCATION: (103)..(103)
<223> OTHER INFORMATION: Xaa at position 103 may be Ile or Val
<220> FEATURE:
<221> NAME/KEY: MISC_FEATURE
<222> LOCATION: (111)..(111)
<223> OTHER INFORMATION: Xaa at position 111 may be Phe or Tyr

<400> SEQUENCE: 8

Gln Val Xaa Xaa Gln Gln Ser Gly Ala Glu Leu Ala Xaa Pro Gly Ala
1               5                   10                  15

Ser Val Lys Met Ser Cys Lys Ala Ser Gly Tyr Ile Phe Thr Ser Tyr
            20                  25                  30

Trp Xaa His Trp Xaa Lys Gln Arg Pro Gly Gln Gly Leu Glu Trp Ile
        35                  40                  45

Gly Tyr Ile Asn Pro Ser Ser Xaa Tyr Xaa Glu Tyr Xaa Xaa Lys Phe
    50                  55                  60

Xaa Asp Lys Ala Thr Leu Thr Ala Asp Xaa Xaa Ser Xaa Thr Ala Tyr
65                  70                  75                  80

Met Xaa Leu Xaa Ser Leu Thr Ser Glu Asp Ser Ala Val Tyr Tyr Cys
            85                  90                  95

Ala Arg Ser Gly Trp Leu Xaa His Gly Asp Tyr Tyr Phe Asp Xaa Trp
            100                 105                 110

Gly Gln Gly Thr Thr Leu Thr Val Ser Ser
        115                 120

<210> SEQ ID NO 9
<211> LENGTH: 17
<212> TYPE: PRT
<213> ORGANISM: Mus musculus

<400> SEQUENCE: 9

Lys Ser Ser Gln Ser Leu Leu Asn Ser Arg Thr Arg Lys Asn Tyr Leu
1               5                   10                  15

Ala

<210> SEQ ID NO 10
<211> LENGTH: 8
<212> TYPE: PRT
<213> ORGANISM: Mus Musculus

<400> SEQUENCE: 10

Gln Gln Ser Tyr Asp Val Val Thr
1               5

<210> SEQ ID NO 11
<211> LENGTH: 20
<212> TYPE: PRT
<213> ORGANISM: Mus Musculus

<400> SEQUENCE: 11

Met Asp Ser Gln Ala Gln Val Leu Ile Leu Leu Leu Leu Trp Val Ser
1               5                   10                  15

Gly Thr Phe Gly
            20

<210> SEQ ID NO 12
```

<211> LENGTH: 132
<212> TYPE: PRT
<213> ORGANISM: Mus Musculus

<400> SEQUENCE: 12

```
Met Asp Ser Gln Ala Gln Val Leu Ile Leu Leu Leu Trp Val Ser
1               5                   10                  15

Gly Thr Phe Gly Asp Ile Val Met Ser Gln Ser Pro Ser Ser Leu Ala
                20                  25                  30

Val Ser Ala Gly Glu Lys Val Thr Met Ser Cys Lys Ser Ser Gln Ser
                35                  40                  45

Leu Leu Asn Ser Arg Thr Arg Lys Asn Tyr Leu Ala Trp Tyr Gln Gln
            50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
                100                 105                 110

Tyr Cys Gln Gln Ser Tyr Asp Val Val Thr Phe Gly Ala Gly Thr Lys
            115                 120                 125

Leu Glu Leu Lys
        130
```

<210> SEQ ID NO 13
<211> LENGTH: 112
<212> TYPE: PRT
<213> ORGANISM: Mus Musculus

<400> SEQUENCE: 13

```
Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Ser Tyr Asp Val Val Thr Phe Gly Ala Gly Thr Lys Leu Glu Leu Lys
                100                 105                 110
```

<210> SEQ ID NO 14
<211> LENGTH: 5
<212> TYPE: PRT
<213> ORGANISM: Mus Musculus

<400> SEQUENCE: 14

```
Ser Tyr Trp Met His
1               5
```

<210> SEQ ID NO 15
<211> LENGTH: 10
<212> TYPE: PRT
<213> ORGANISM: Mus Musculus

<400> SEQUENCE: 15

Gly Tyr Ile Phe Thr Ser Tyr Trp Met His
1               5                   10

<210> SEQ ID NO 16
<211> LENGTH: 17
<212> TYPE: PRT
<213> ORGANISM: Mus Musculus

<400> SEQUENCE: 16

Tyr Ile Asn Pro Ser Ser Asp Tyr Asn Glu Tyr Ser Glu Lys Phe Met
1               5                   10                  15

Asp

<210> SEQ ID NO 17
<211> LENGTH: 13
<212> TYPE: PRT
<213> ORGANISM: Mus Musculus

<400> SEQUENCE: 17

Ser Gly Trp Leu Val His Gly Asp Tyr Tyr Phe Asp Tyr
1               5                   10

<210> SEQ ID NO 18
<211> LENGTH: 19
<212> TYPE: PRT
<213> ORGANISM: Mus Musculus

<400> SEQUENCE: 18

Met Glu Arg His Trp Ile Phe Leu Phe Leu Phe Ser Val Thr Ala Gly
1               5                   10                  15

Val His Ser

<210> SEQ ID NO 19
<211> LENGTH: 141
<212> TYPE: PRT
<213> ORGANISM: Mus Musculus

<400> SEQUENCE: 19

Met Glu Arg His Trp Ile Phe Leu Phe Leu Phe Ser Val Thr Ala Gly
1               5                   10                  15

Val His Ser Gln Val Gln Val Gln Gln Ser Gly Ala Glu Leu Ala Glu
                20                  25                  30

Pro Gly Ala Ser Val Lys Met Ser Cys Lys Ala Ser Gly Tyr Ile Phe
            35                  40                  45

Thr Ser Tyr Trp Met His Trp Leu Lys Gln Arg Pro Gly Gln Gly Leu
    50                  55                  60

Glu Trp Ile Gly Tyr Ile Asn Pro Ser Ser Asp Tyr Asn Glu Tyr Ser
65                  70                  75                  80

Glu Lys Phe Met Asp Lys Ala Thr Leu Thr Ala Asp Lys Ala Ser Thr
                85                  90                  95

Thr Ala Tyr Met Gln Leu Ile Ser Leu Thr Ser Glu Asp Ser Ala Val
            100                 105                 110

Tyr Tyr Cys Ala Arg Ser Gly Trp Leu Val His Gly Asp Tyr Tyr Phe
        115                 120                 125

Asp Tyr Trp Gly Gln Gly Thr Thr Leu Thr Val Ser Ser
    130                 135                 140

<210> SEQ ID NO 20

```
<211> LENGTH: 122
<212> TYPE: PRT
<213> ORGANISM: Mus Musculus

<400> SEQUENCE: 20

Gln Val Gln Val Gln Gln Ser Gly Ala Glu Leu Ala Glu Pro Gly Ala
1               5                   10                  15

Ser Val Lys Met Ser Cys Lys Ala Ser Gly Tyr Ile Phe Thr Ser Tyr
            20                  25                  30

Trp Met His Trp Leu Lys Gln Arg Pro Gly Gln Gly Leu Glu Trp Ile
        35                  40                  45

Gly Tyr Ile Asn Pro Ser Ser Asp Tyr Asn Glu Tyr Ser Glu Lys Phe
    50                  55                  60

Met Asp Lys Ala Thr Leu Thr Ala Asp Lys Ala Ser Thr Thr Ala Tyr
65                  70                  75                  80

Met Gln Leu Ile Ser Leu Thr Ser Glu Asp Ser Ala Val Tyr Tyr Cys
                85                  90                  95

Ala Arg Ser Gly Trp Leu Val His Gly Asp Tyr Tyr Phe Asp Tyr Trp
            100                 105                 110

Gly Gln Gly Thr Thr Leu Thr Val Ser Ser
        115                 120

<210> SEQ ID NO 21
<211> LENGTH: 17
<212> TYPE: PRT
<213> ORGANISM: Mus Musculus

<400> SEQUENCE: 21

Lys Ser Ser Gln Ser Leu Leu His Thr Ser Thr Arg Lys Asn Tyr Leu
1               5                   10                  15

Ala

<210> SEQ ID NO 22
<211> LENGTH: 8
<212> TYPE: PRT
<213> ORGANISM: Mus Musculus

<400> SEQUENCE: 22

Lys Gln Ser Tyr Asp Val Val Thr
1               5

<210> SEQ ID NO 23
<211> LENGTH: 20
<212> TYPE: PRT
<213> ORGANISM: Mus Musculus

<400> SEQUENCE: 23

Met Asp Ser Gln Ala Gln Val Leu Ile Leu Leu Leu Leu Trp Val Ser
1               5                   10                  15

Gly Thr Cys Gly
            20

<210> SEQ ID NO 24
<211> LENGTH: 132
<212> TYPE: PRT
<213> ORGANISM: Mus Musculus

<400> SEQUENCE: 24

Met Asp Ser Gln Ala Gln Val Leu Ile Leu Leu Leu Leu Trp Val Ser
1               5                   10                  15
```

```
Gly Thr Cys Gly Asp Ile Val Met Ser Gln Ser Pro Ser Ser Leu Ala
            20                  25                  30

Val Ser Ala Gly Glu Lys Val Thr Met Thr Cys Lys Ser Ser Gln Ser
        35                  40                  45

Leu Leu His Thr Ser Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asp Val Val Thr Phe Gly Ala Gly Thr Lys
        115                 120                 125

Leu Glu Leu Lys
    130

<210> SEQ ID NO 25
<211> LENGTH: 112
<212> TYPE: PRT
<213> ORGANISM: Mus Musculus

<400> SEQUENCE: 25

Asp Ile Val Met Ser Gln Ser Pro Ser Ser Leu Ala Val Ser Ala Gly
1               5                   10                  15

Glu Lys Val Thr Met Thr Cys Lys Ser Ser Gln Ser Leu Leu His Thr
            20                  25                  30

Ser Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asp Val Val Thr Phe Gly Ala Gly Thr Lys Leu Glu Leu Lys
            100                 105                 110

<210> SEQ ID NO 26
<211> LENGTH: 5
<212> TYPE: PRT
<213> ORGANISM: Mus Musculus

<400> SEQUENCE: 26

Ser Tyr Trp Ile His
1               5

<210> SEQ ID NO 27
<211> LENGTH: 10
<212> TYPE: PRT
<213> ORGANISM: Mus Musculus

<400> SEQUENCE: 27

Gly Thr Thr Phe Thr Ser Tyr Trp Ile His
1               5                   10

<210> SEQ ID NO 28
<211> LENGTH: 17
<212> TYPE: PRT
```

-continued

<213> ORGANISM: Mus Musculus

<400> SEQUENCE: 28

Tyr Ile Asn Pro Ser Ser Gly Tyr His Glu Tyr Asn Gln Lys Phe Ile
1               5                   10                  15

Asp

<210> SEQ ID NO 29
<211> LENGTH: 13
<212> TYPE: PRT
<213> ORGANISM: Mus Musculus

<400> SEQUENCE: 29

Ser Gly Trp Leu Ile His Gly Asp Tyr Tyr Phe Asp Phe
1               5                   10

<210> SEQ ID NO 30
<211> LENGTH: 19
<212> TYPE: PRT
<213> ORGANISM: Mus Musculus

<400> SEQUENCE: 30

Met Glu Arg His Trp Ile Phe Leu Phe Leu Phe Ser Val Thr Ala Gly
1               5                   10                  15

Val His Ser

<210> SEQ ID NO 31
<211> LENGTH: 141
<212> TYPE: PRT
<213> ORGANISM: Mus Musculus

<400> SEQUENCE: 31

Met Glu Arg His Trp Ile Phe Leu Phe Leu Phe Ser Val Thr Ala Gly
1               5                   10                  15

Val His Ser Gln Val His Leu Gln Gln Ser Gly Ala Glu Leu Ala Lys
            20                  25                  30

Pro Gly Ala Ser Val Lys Met Ser Cys Lys Ala Ser Gly Tyr Thr Phe
        35                  40                  45

Thr Ser Tyr Trp Ile His Trp Ile Lys Gln Arg Pro Gly Gln Gly Leu
    50                  55                  60

Glu Trp Ile Gly Tyr Ile Asn Pro Ser Ser Gly Tyr His Glu Tyr Asn
65                  70                  75                  80

Gln Lys Phe Ile Asp Lys Ala Thr Leu Thr Ala Asp Arg Ser Ser Ser
                85                  90                  95

Thr Ala Tyr Met His Leu Thr Ser Leu Thr Ser Glu Asp Ser Ala Val
            100                 105                 110

Tyr Tyr Cys Ala Arg Ser Gly Trp Leu Ile His Gly Asp Tyr Tyr Phe
        115                 120                 125

Asp Phe Trp Gly Gln Gly Thr Thr Leu Thr Val Ser Ser
    130                 135                 140

<210> SEQ ID NO 32
<211> LENGTH: 122
<212> TYPE: PRT
<213> ORGANISM: Mus Musculus
<220> FEATURE:
<221> NAME/KEY: MISC_FEATURE
<222> LOCATION: (1)..(1)
<223> OTHER INFORMATION: Xaa at position 1 may be Gln or Pyro-Glutamate

<400> SEQUENCE: 32

```
Xaa Val His Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
                20                  25                  30

Trp Ile His Trp Ile Lys Gln Arg Pro Gly Gln Gly Leu Glu Trp Ile
            35                  40                  45

Gly Tyr Ile Asn Pro Ser Ser Gly Tyr His Glu Tyr Asn Gln Lys Phe
        50                  55                  60

Ile Asp Lys Ala Thr Leu Thr Ala Asp Arg Ser Ser Thr Ala Tyr
65                  70                  75                  80

Met His Leu Thr Ser Leu Thr Ser Glu Asp Ser Ala Val Tyr Tyr Cys
                85                  90                  95

Ala Arg Ser Gly Trp Leu Ile His Gly Asp Tyr Tyr Phe Asp Phe Trp
                100                 105                 110

Gly Gln Gly Thr Thr Leu Thr Val Ser Ser
            115                 120
```

<210> SEQ ID NO 33
<211> LENGTH: 396
<212> TYPE: DNA
<213> ORGANISM: Mus Musculus

<400> SEQUENCE: 33

| | |
|---|---:|
| atggattcac aggcccaggt tcttatattg ctgctgctat gggtatctgg tacctttggg | 60 |
| gacattgtga tgtcacaatc tccatcctcc ctggctgtgt cagcaggaga gaaggtcact | 120 |
| atgagctgca aatccagtca gagtctgctc aacagtagaa cccgaaagaa ctacttggct | 180 |
| tggtaccagc agaaaccagg gcagtctcct aaactgctga tctactgggc atccactagg | 240 |
| gaatctgggg tccctgatcg cttcacaggc agtggatctg gacagattt cactctcacc | 300 |
| atcagcagtg tgcaggctga agacctggca gtttattact gccagcaatc ttatgatgtg | 360 |
| gtcacgttcg gtgctgggac caagctggag ctgaaa | 396 |

<210> SEQ ID NO 34
<211> LENGTH: 423
<212> TYPE: DNA
<213> ORGANISM: Mus Musculus

<400> SEQUENCE: 34

| | |
|---|---:|
| atggaaaggc actggatctt tctcttcctg ttttcagtaa ctgcaggtgt ccactcccag | 60 |
| gtccaggttc agcagtctgg ggctgaactg gcagaacctg gggcctcagt gaagatgtcc | 120 |
| tgcaaggcct ctggctacat ctttactagc tactggatgc actggctaaa gcagaggcct | 180 |
| ggacagggtc tggaatggat tggatacatt aatcccagca gtgattataa tgaatacagt | 240 |
| gagaaattca tggacaaggc cacattgact gcagacaaag cctccaccac agcctacatg | 300 |
| caactgatca gcctgacatc tgaggactct gcagtctatt actgtgcaag atcgggatgg | 360 |
| ttagtacatg gagactatta ttttgactac tggggccaag gcaccactct cacagtctcc | 420 |
| tca | 423 |

<210> SEQ ID NO 35
<211> LENGTH: 396
<212> TYPE: DNA
<213> ORGANISM: Mus Musculus

<400> SEQUENCE: 35

```
atggattcac aggcccaggt tcttatattg ctgctgctat gggtatctgg tacctgtggg        60
gacattgtga tgtcacagtc tcctcctcc ctggctgtgt cagcaggaga gaaggtcact        120
atgacctgca aatccagtca gagtctgctc cacactagca cccgaaagaa ctacttggct      180
tggtaccagc agaaaccagg gcagtctcct aaactgctga tctattgggc atccactagg      240
gaatctgggg tccctgatcg cttcacaggc agtggatctg ggacagattt cactctcacc      300
atcagcagtg tgcaggctga agacctggca gtttattact gcaaacaatc ttatgatgtg      360
gtcacgttcg gtgctgggac caagctggag ctgaaa                                 396

<210> SEQ ID NO 36
<211> LENGTH: 423
<212> TYPE: DNA
<213> ORGANISM: Mus Musculus

<400> SEQUENCE: 36
atggaaaggc actggatctt tctcttcctg ttttcagtaa ctgcaggtgt ccactcccag       60
gtccaccttc agcagtctgg ggctgaactg gcaaaacctg gggcctcagt gaagatgtcc      120
tgcaaggctt ctggctacac gtttactagt tactggatac actggataaa gcagaggcct     180
ggacagggtc tggaatggat tggatacatt aatccttcct ctggttatca tgaatacaat     240
cagaaattca ttgacaaggc cacattgact gctgacagat cctccagcac agcctacatg    300
cacctgacca gcctgacgtc tgaagactct gcagtctatt actgtgcaag atcgggatgg    360
ttaatacatg gagactacta ctttgacttc tggggccaag gcaccactct cacagtctcc    420
tca                                                                  423
```

ANTIBODIES THAT BIND TO HUMAN PROGRAMMED DEATH LIGAND 1 (PD-L1)

CROSS REFERENCE TO RELATED APPLICATIONS

This application is a National Stage of International Application No. PCT/US2013/075932, filed on Dec. 18, 2013, which claims the benefit under 35 U.S.C. 119(e) of U.S. Provisional Application No. 61/745,386, filed Dec. 21, 2012.

REFERENCE TO SEQUENCE LISTING SUBMITTED ELECTRONICALLY

The sequence listing of the present application is submitted electronically via EFS-Web as an ASCII formatted sequence listing with a file name "23411_US_PCT_SEQ_LIST.TXT", creation date of Jun. 18, 2015, and a size of 22 KB. This sequence listing submitted via EFS-Web is part of the specification and is herein incorporated by reference in its entirety.

FIELD OF THE INVENTION

The present invention relates to antibodies having specific sequences that bind to human Programmed Death Ligand 1 (PD-L1) and are useful for detecting PD-L1 expression in human tissue samples by immunohistochemical (IHC) analysis. The invention also relates to specific IHC assays that employ these anti-human-PD-L1 Antibodies.

BACKGROUND OF THE INVENTION

PD-L1 is a cell surface glycoprotein that is one of two known ligands for Programmed Death 1 (PD-1), which is recognized as an important player in immune regulation and the maintenance of peripheral tolerance. Expression of PD-L1 has been observed on the surface of a variety of immune cells, including naive lymphocytes and activated B and T cells, monocytes and dendritic cells (Id.). Furthermore, PD-L1 mRNA is expressed by non-lymphoid tissues including vascular endothelial cells, epithelial cells, muscle cells, and in tonsil and placental tissue. See, e.g., Keir, M. E. et al., *Annu Rev Immunol.* 26:677-704 (2008); Sharp A. H. et al., *Nature Immunol.* 8:239-245 (2007); Okazaki T and Honjo T, *Internat. immunol.* 19:813-824 (2007).

PD-L1 expression has also been observed in a variety of human cancers, and interaction of tumor-cell expressed PD-L1 with PD-1 can induce inhibition or apoptosis of tumor-specific T cells. In large sample sets of e.g. ovarian, renal, colorectal, pancreatic, liver cancers and melanoma it was shown that PD-L1 expression correlated with poor prognosis and reduced overall survival irrespective of subsequent treatment. Anti-PD-1 monoclonal antibodies that block binding of PD-L1 to PD-1 have been shown to have anti-tumor activity against a variety of tumor types, with early human clinical data suggesting that patients whose tumors express PD-L1 are more likely to respond to anti-PD-1 therapy. See, e.g., Iwai et al., *PNAS* 99:12293-12297 (2002); Ohigashi et al., *Clin Cancer Res* 11:2947-2953 (2005); Ghebeh et al., *Neoplasia* 8:190-198 (2006); Hamanishi, J et al., *PNAS* 104:3360-3365 (2007); Yang et al., *Invest Ophthalmol Vis Sci.* 49(6):2518-2525 (2008); Gao et al., *Clin Cancer Res* 15:971-979 (2009); Brahmer J. R. et al., *J Clin Oncol.* 28:3167-3175 (2010).

A recent report describes the comparison of 15 anti-human PD-L1 antibodies for utility in detecting expression of hPD-L1 in formalin-fixed paraffin-embedded (FFPE) human melanoma samples (Gadiot, J., et al., *Cancer* 117 (10):2192-2201 (2011)). The utility criteria assessed in this comparison were: (1) ability to stain paraffin-embedded tissues, (2) produce low background staining, and (3) blocked binding to PD-L1 by pre-incubation with a PD-L1 fusion protein. The authors concluded that Ab #4059, a rabbit anti-human polyclonal antibody (obtained from ProSci, Poway, Calif. USA), was the only anti-human PD-L1 antibody of the 15 tested to acceptably meet all of these criteria (Id. at 2195, $2^{nd}$ column).

SUMMARY OF THE INVENTION

The present invention relates to anti-human PD-L1 monoclonal antibodies, which produce an IHC staining pattern in FFPE tonsil tissue that the inventors herein believe to be more immunologically relevant than that produced by the ProSci Ab #4059. As described in the Examples below, the inventors found that this ProSci antibody (PRS4059, Sigma-Aldrich lot 40590604) stained all of the hematopoeitic lineages in the tonsil with equal intensity, whereas two antibodies of the present invention, 22C3 and 20C3, selectively stained tonsil crypt epithelium and follicular CD68+ myeloid cells, which are morphologically consistent with macrophages. Moreover, 22C3 and 20C3 demonstrate a consistent intensity difference between these two discrete cell populations with staining intensity in crypt epithelium being much greater than in follicular macrophages. All three antibodies (PRS4059, 22C3 and 20C3) are neutralized with pre-incubation with the PD-L1 antigen, indicating that the reactivity is mediated by the antigen-binding domain (CDRs). Thus, the invention also relates to use of the antibodies of the present invention in the detection of PD-L1 expression on the surface of human cells, including in IHC assays to detect PD-L1 in FFPE tissue sections.

In one aspect, the invention provides an isolated antibody, or an antigen binding fragment thereof, that specifically binds to human PD-L1. The isolated monoclonal antibody, or antigen binding fragment thereof, comprises three light chain CDRs of CDRL1, CDRL2 and CDRL3 and three heavy chain CDRs of CDRH1, CDRH2 and CDRH3.

CDRL1 is selected from the group consisting of SEQ ID NO:1, SEQ ID NO:9, SEQ ID NO:21, a variant of SEQ ID NO:9, and a variant of SEQ ID NO:21. CDRL2 is selected from the group consisting of SEQ ID NO:2 and a variant of SEQ ID NO:2. CDRL3 is selected from the group consisting of SEQ ID NO:3, SEQ ID NO:10, SEQ ID NO:22, a variant of SEQ ID NO:10, and a variant of SEQ ID NO:22.

CDRH1 is selected from the group consisting of SEQ ID NO:5, SEQ ID NO:14, SEQ ID NO:15, SEQ ID NO:26, SEQ ID NO:27, a variant of SEQ ID NO:14, a variant of SEQ ID NO:15, a variant of SEQ ID NO:26, and a variant of SEQ ID NO:27. CDRH2 is selected from the group consisting of SEQ ID NO:6, SEQ ID NO:16, SEQ ID NO:28, a variant of SEQ ID NOs:16, and a variant of SEQ ID NO:28. CDRH3 is selected from the group consisting of SEQ ID NO:7, SEQ ID NO:17, SEQ ID NO:29, a variant of SEQ ID NOs:17, and a variant of SEQ ID NO:29.

In antibodies and antigen binding fragments of the invention, a variant CDR sequence (light chain or heavy chain) is identical to the reference sequence except having one or two conservative amino acid substitutions in the reference sequence, and preferably has only one conservative amino acid substitution in the reference sequence. In preferred embodiments, at most two of the three light chain CDRs are a variant sequence, and at most two of the three heavy chain CDRs are a variant sequence. In more preferred embodiments, only three, two or one of the six CDRs are variant sequences.

In one preferred embodiment, the three light chain CDRs are SEQ ID NO:1, SEQ ID NO:2, and SEQ ID NO:3 and the three heavy chain CDRs are SEQ ID NO:5, SEQ ID NO:6 and SEQ ID NO:7.

In another preferred embodiment, the three light chain CDRs are SEQ ID NO:9, SEQ ID NO:2, and SEQ ID NO:10 and the three heavy chain CDRs are SEQ ID NO:14, SEQ ID NO:16 and SEQ ID NO:17.

In yet another preferred embodiment, the three light chain CDRs are SEQ ID NO:21, SEQ ID NO:2 and SEQ ID NO:22 and the three heavy chain CDRs are SEQ ID NO:26, SEQ ID NO:28 and SEQ ID NO:29.

Some antibody and antigen binding fragments of the invention comprise a light chain variable region and a heavy chain variable region. The light chain variable region is selected from the group consisting of SEQ ID NO:4, SEQ ID NO:13, a variant of SEQ ID NO:13, SEQ ID NO:25 and a variant of SEQ ID NO:25, and the heavy chain variable region is selected from the group consisting of SEQ ID NO:8, SEQ ID NO:20, a variant of SEQ ID NO:20, SEQ ID NO:32 and a variant of SEQ ID NO:32. In such embodiments, a variant light chain variable region sequence is identical to the reference sequence except having up to five conservative amino acid substitutions in the framework region (i.e., outside of the CDRs), and preferably has less than four, three or two conservative amino acid substitution in the framework region. Similarly, a variant heavy chain variable region sequence is identical to the reference sequence except having up to 17 conservative amino acid substitutions in the framework region (i.e., outside of the CDRs), and preferably has less than ten, nine, eight, seven, six or five conservative amino acid substitutions in the framework region.

In one preferred antibody or antigen binding fragment of the invention, the light chain variable region is SEQ ID NO:13 and the heavy chain variable region is SEQ ID NO:20.

Another preferred antibody or antigen binding fragment of the invention comprises a light chain variable region of SEQ ID NO:25 and a heavy chain variable region of SEQ ID NO:32.

In yet another embodiment, the antibody or binding fragment of the invention comprises a light chain variable region of SEQ ID NO:25 and a heavy chain variable region of SEQ ID NO:32, wherein X in SEQ ID NO:32 is pE.

In a still further embodiment, the antibody or binding fragment of the invention comprises a light chain variable region of SEQ ID NO:25 and a heavy chain variable region of SEQ ID NO:32, wherein X in SEQ ID NO:32 is Q.

In all of the above antibody embodiments, the isolated antibody may be a full-length antibody of any class of immunoglobulin, including IgM, IgG, IgD, IgA, and IgE. Preferably, the antibody is an IgG antibody, such as $IgG_1$, $IgG_2$, $IgG_3$, or $IgG_4$. In one embodiment, the antibody comprises a mouse $IgG_1$ constant region.

Particularly preferred antibodies are monoclonal antibodies 20C3 and 22C3, which are IgG1 antibodies expressed by hybridomas MEB037.20C3 and MEB037.22C3, respectively.

The invention also provides an isolated monoclonal antibody, or an antigen binding fragment thereof, which specifically binds to human PD-L1 and blocks the binding to human PD-L1 of 20C3 or 22C3, or of a reference antibody that comprises SEQ ID NO:25 and SEQ ID NO:32. In one preferred embodiment, an antibody or antigen binding fragment of the invention blocks binding to human PD-L1 of each of 20C3 and 22C3, or of each of (a) a reference antibody that comprises SEQ ID NO:13 and SEQ ID NO:20 and (b) a reference antibody that comprises SEQ ID NO:25 and SEQ ID NO:32.

The invention also provides an antibody composition, which comprises any of the above-described antibodies or antibody fragments in a formulation. One suitable formulation comprises 20 mM sodium acetate and 9% sucrose at pH 5.0. In a preferred embodiment, the composition comprises a mixture of antibody molecules, in which a majority (i.e., more than any of 60%, 65%, 70%, 80%, 85%, 90% or 95%) of the antibody molecules in the mixture comprise SEQ ID NO:25 and SEQ ID NO:32, wherein X in SEQ ID NO:32 is pE, and the remainder of the antibody molecules in the mixture comprise SEQ ID NO:25 and SEQ ID NO:32, wherein X in SEQ ID NO:32 is Q.

In any of the above embodiments, the antigen binding fragment is a Fab fragment, a Fab' fragment, a $(Fab')_2$ fragment.

In any of the above embodiments, the antibody or antigen binding fragment may further comprise a detectable label.

The invention also provides an isolated nucleic acid encoding any of the antibody variable regions disclosed above. In one preferred embodiment, the nucleic acid comprises one or both of SEQ ID NO:33 and SEQ ID NO:34. In another preferred embodiment, the nucleic acid comprises one or both of SEQ ID NO:35 and SEQ ID NO:36. In any of these embodiments, the isolated nucleic acid is preferably an expression vector.

The invention also relates to a host cell comprising an expression vector that encodes any of the antibody variable regions disclosed above. Preferably, the expression vector comprises SEQ ID NO:33 and SEQ ID NO:34 or comprises SEQ ID NO:35 and SEQ ID NO:36.

The invention also provides a method of assaying a human tissue sample that has been removed from a human for PD-L1 expression. The assay method comprises contacting the tissue sample with a PD-L1 binding reagent under conditions that allow specific binding of the PD-L1 binding reagent to human PD-L1, removing unbound PD-L1 binding reagent, and detecting the presence or absence of bound PD-L1 binding agent. In one preferred embodiment, the method further comprises quantifying the amount of bound binding reagent. The binding reagent is any of the monoclonal antibody or antigen binding fragments described above. Preferably, the binding reagent is an antibody which comprises SEQ ID NO:13 and SEQ ID NO:20, or comprises SEQ ID NO:25 and SEQ ID NO:32. In one preferred embodiment, the binding reagent is an antibody composition which comprises a mixture of antibody molecules comprising SEQ ID NO:25 and SEQ ID NO:32, wherein a majority of the molecules (i.e., more than any of 60%, 65%, 70%, 80%, 85%, 90% or 95%) have pE at position X in SEQ ID NO:32 and the remainder of the molecules have Q at position X in SEQ ID NO:32.

In another aspect, the invention provides a kit for assaying a human tissue sample for PD-L1 expression. The kit comprises a PD-L1 binding agent and a set of reagents for detecting a complex comprising the binding agent bound to human PD-L1. The PD-L1 binding agent is any monoclonal antibody or antigen binding fragment described above that specifically binds to human PD-L1. Preferably, the antibody or binding fragment comprises SEQ ID NO:13 and SEQ ID NO:20, or comprises SEQ ID NO:25 and SEQ ID NO:32. In one preferred embodiment, the binding reagent is an antibody composition which comprises a mixture of antibody molecules comprising SEQ ID NO:25 and SEQ ID NO:32, wherein a majority of the molecules (i.e., more than any of 60%, 65%, 70%, 80%, 85%, 90% or 95%) have pE at position X in SEQ ID NO:32 and the remainder of the molecules have Q at position X in SEQ ID NO:32.

BRIEF DESCRIPTION OF THE DRAWINGS

FIG. 1 shows the nucleotide sequences for antibody variable heavy (SEQ ID NO:34) and light (SEQ ID NO:33) chain cDNA prepared from total RNA isolated from hybridoma MEB037.20C3 and the predicted amino acid sequences encoded thereby (bold font, SEQ ID NOs:19 and 12, respectively), with brackets indicating nucleotide and amino acid sequences for the leader peptide and underlining indicating the CDR sequences.

FIG. 2 shows the nucleotide sequences for antibody variable heavy (SEQ ID NO:36) and light (SEQ ID NO:35) chain cDNA prepared from total RNA isolated from hybridoma MEB037.22C3 and the predicted amino acid sequences encoded thereby (bold font, SEQ ID NOs:31 and 24, respectively), with brackets indicating nucleotide and amino acid sequences for the leader peptide and underlining indicating the CDR sequences.

FIG. 3 shows the aligned amino acid sequences for the mature variable regions of the light (SEQ ID NOs:13 and 25) and heavy chains (SEQ ID NOs: 20 and 32) of antibodies 20C3 and 22C3, with bold font indicating the positions where the sequences vary, underlining indicating the CDR sequences, as defined by the Kabat numbering system, and brackets indicating the heavy chain CDR1 as defined by the Chothia numbering system.

FIG. 7 shows the IHC staining produced by antibody 22C3 on FFPE cell pellets of engineered CHO cell lines (FIG. 7A) and human cell lines (FIG. 7B, top panel), and demonstrates that the staining intensity correlates well with hPD-L1 mRNA expression levels measured in the same human cell lines (FIG. 7B, bottom panel).

DETAILED DESCRIPTION

Figure 4A:
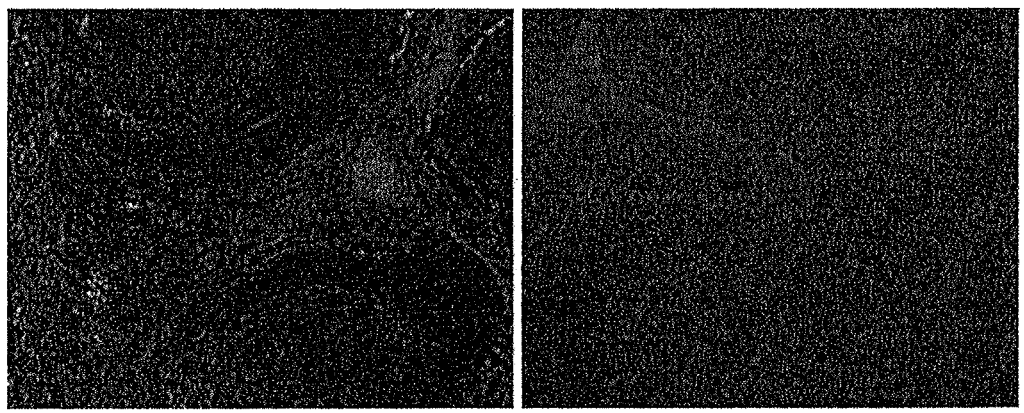
FIG. 4 shows staining of tonsil sections produced by immunohistical assay using the commercially available antibody PRS4059 (FIG. 4A) or the 22C3 antibody of the invention (FIG. 4B), with the sections on the right side of FIGS. 4A and 4B showing the results after pre-incubation with a PD-L1-IgG1 fusion protein (R&D Systems), which competes with the anti-human PD-L1 antibodies for binding to human PD-L1.

Abbreviations. Throughout the detailed description and examples of the invention the following abbreviations will be used:
ADCC Antibody-dependent cellular cytotoxicity
CDC Complement-dependent cytotoxicity
CDR Complementarity determining region in the immunoglobulin variable regions, defined using the Kabat numbering system, unless otherwise indicated
CHO Chinese hamster ovary
Clothia An antibody numbering system described in Al-Lazikani et al., *JMB* 273:927-948 (1997)
EC50 concentration resulting in 50% efficacy or binding
ELISA Enzyme-linked immunosorbant assay
FFPE formalin-fixed, paraffin-embedded
FR Antibody framework region: the immunoglobulin variable regions excluding the CDR regions.
HRP Horseradish peroxidase
IFN interferon
IC50 concentration resulting in 50% inhibition
IgG Immunoglobulin G
Kabat An immunoglobulin alignment and numbering system pioneered by Elvin A. Kabat ((1991) Sequences of Proteins of Immunological Interest, 5th Ed. Public Health Service, National Institutes of Health, Bethesda, Md.)
mAb or Mab or MAb Monoclonal antibody
MES 2-(N-morpholino)ethanesulfonic acid
MOA Mechanism of action
NHS Normal human serum
PCR Polymerase chain reaction
pE Pyro-glutamate
PK Pharmacokinetics
SEB Staphylococcus Enterotoxin B
TT Tetanus toxoid
V region The segment of IgG chains which is variable in sequence between different antibodies. It extends to Kabat residue 109 in the light chain and 113 in the heavy chain.
VH Immunoglobulin heavy chain variable region
VK Immunoglobulin kappa light chain variable region Definitions So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Activation" as it applies to cells or to receptors refers to the activation or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Activity" may refer to modulation of components of the innate or the adaptive immune systems.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human.

"Treat" or "treating" means to administer a therapeutic agent, such as a composition containing any of the antibodies or antigen binding fragments of the present invention, internally or externally to a subject or patient having one or more disease symptoms, or being suspected of having a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the chi$^r$-test, the U-test according to Mann and Whitney, the Kruskal-Wallis test (H-test), Jonckheere-Terpstra-test and the Wilcoxon-test.

"Treatment," as it applies to a human, veterinary, or research subject, refers to therapeutic treatment, as well as research and diagnostic applications. "Treatment" as it applies to a human, veterinary, or research subject, or cell, tissue, or organ, encompasses contact of the antibodies or antigen binding fragments of the present invention to a human or animal subject, a cell, tissue, physiological compartment, or physiological fluid.

Anti-PD-L1 Antibodies

Antibody 20C3 is the antibody produced by hybridoma subclone MEB037.20C3.116.

Antibody 22C3 is the antibody produced by hybridoma subclone MEB037.22C3.138, and corresponds to the allotype S414R of a mouse IgG1. The N-terminal residue of the mature heavy chain of 22C3 is either glutamine or gyroglutamate (pE), which is a common post-translational modification that is frequently observed in monoclonal antibodies when the gene sequence codes for an N-terminal glutamine in the mature heavy or light chain.

The antibodies and antigen binding fragments of the present invention bind to the mature form of human PD-L1 (lacking the presecretory leader sequence, also referred to as leader peptide) that is expressed on the surface of certain human cells. The terms "PD-L1" and "mature PD-L1" are used interchangeably herein, and shall be understood to mean the same molecule unless otherwise indicated or readily apparent from the context. A mature human PD-L1 molecule consists of amino acids 19-290 of the following sequence

```
(SEQ ID NO: 37):
MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET.
```

The extracellular domain of mature human PD-L1 consists of the following sequence

```
(SEQ ID NO: 38):
FTVTVPKDLYVVEYGSNMTIECKFPVEKQLDLAALIVYWEMEDKNIIQFV

HGEEDLKVQHSSYRQRARLLKDQLSLGNAALQITDVKLQDAGVYRCMISY

GGADYKRITVKVNAPYNKINQRILVVDPVTSEHELTCQAEGYPKAEVIWT

SSDHQVLSGKTTTTNSKREEKLFNVTSTLRINTTTNEIFYCTFRRLDPEE

NHTAELVIPELPLAHPPNERT.
```

As used herein, an anti-human PD-L1 antibody or an anti-hPD-L1 antibody refers to an antibody that specifically binds to human PD-L1. An antibody that "specifically binds to human PD-L1," or an antibody that "specifically binds to a polypeptide comprising the amino acid sequence of human PD-L1," is an antibody that exhibits preferential binding to human PD-L1 as compared to other antigens, but this specificity does not require absolute binding specificity. An anti-hPD-L1 antibody is considered "specific" for human PD-L1 if its binding is determinative of the presence of human PD-L1 in a sample, e.g. without producing undesired results such as false positives in an IHC diagnostic assay. The degree of specificity necessary for an anti-hPD-L1 antibody of the invention may depend on the intended use of the antibody, and at any rate is defined by its suitability for use for an intended purpose. The antibody, or binding fragment thereof, of the invention binds to human PD-L1 with an affinity that is at least two fold greater, preferably at least ten times greater, more preferably at least 20-times greater, and most preferably at least 100-times greater than the affinity with any non-PD-L1 protein. As used herein, an antibody is said to bind specifically to a polypeptide comprising a given sequence, e.g. mature human PD-L1 (in this case amino acids 19-290 of SEQ ID NO:37), if it binds to polypeptides comprising that sequence but does not bind to proteins lacking that sequence. For example, an antibody that specifically binds to a polypeptide comprising 19-290 of SEQ ID NO:37 may bind to a FLAG®-tagged form of 19-290 of SEQ ID NO:37 but will not bind to other FLAG®-tagged proteins.

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic antibody.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

A "Fab fragment" is comprised of one light chain and the $C_H1$ and variable regions of one heavy chain. The heavy chain of a Fab molecule cannot form a disulfide bond with another heavy chain molecule. An "Fab fragment" can be the product of papain cleavage of an antibody.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H^2$ domains, such that an interchain disulfide bond is formed between the two heavy chains. A F(ab')$_2$ fragment thus is composed of two Fab' fragments that are held together by a disulfide bond between the two heavy chains. An "F(ab')$_2$ fragment" can be the product of pepsin cleavage of an antibody.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun (1994) THE PHARMACOLOGY OF MONOCLONAL ANTIBODIES, vol. 113, Rosenburg and Moore eds. Springer-Verlag, N.Y., pp. 269-315. See also, International Patent Application Publication No. WO 88/01649 and U.S. Pat. Nos. 4,946,778 and 5,260,203.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

In certain embodiments, monoclonal antibodies herein also include camelized single domain antibodies. See, e.g., Muyldermans et al. (2001) Trends Biochem. Sci. 26:230; Reichmann et al. (1999) J. Immunol. Methods 231:25; WO 94/04678; WO 94/25591; U.S. Pat. No. 6,005,079). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) Proc. Natl. Acad. Sci. USA 90: 6444-6448. For a review of engineered antibody variants generally see Holliger and Hudson (2005) Nat. Biotechnol. 23:1126-1136.

Typically, an antibody or antigen binding fragment of the invention retains at least 10% of its human PD-L1 binding activity (when compared to the parental antibody) when that activity is expressed on a molar basis. Preferably, an antibody or antigen binding fragment of the invention retains at least 20%, 50%, 70%, 80%, 90%, 95% or 100% or more of the human PD-L1 binding affinity as the parental antibody. It is also intended that an antibody or antigen binding fragment of the invention can include conservative or non conservative amino acid substitutions (referred to as "conservative variants" or "function conserved variants" of the antibody) that do not substantially alter its biologic activity.

"Isolated antibody" refers to the purification status and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

The term "monoclonal antibody", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). As used herein, the term "framework" or "FR" residues refers to those variable domain residues other than the hypervariable region residues defined herein as CDR residues.

"Homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared×100. For example, if 8 of 10 of the positions in two sequences are matched or homologous when the sequences are optimally aligned then the two sequences are 80% homologous. Generally, the comparison is made when two sequences are aligned to give maximum percent homology. For example, the comparison can be performed by a BLAST algorithm wherein the parameters of the algorithm are selected to give the largest match between the respective sequences over the entire length of the respective reference sequences.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which specific nucleic acid sequences, RNA and/or DNA, are amplified as described in, e.g., U.S. Pat. No. 4,683,195. Generally, sequence information from the ends of the region of interest or beyond is used to design oligonucleotide primers. These primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al. (2005) *Nucleic Acids Res.* 33:D256-D261.

Physical and Functional Properties of the Exemplary Anti-PD-L1 Antibodies

The present invention provides isolated anti-PD-L1 antibodies and methods of use of the antibodies or antigen binding fragments thereof in the detection of PD-L1 expression on the surface of cells. Examples of anti-PD-L1 antibodies of the invention include, but are not limited to: antibodies 20C3 and 22C3 (see FIGS. 1 and 2). The 20C3 and 22C3 antibodies bind non-identical, but adjacent epitopes (see Example 2 and FIG. 9), indicating that the CDRs of these two antibodies can be mixed to derive additional antibodies that specifically bind to PD-L1 at one or both of these epitopes. Thus, the isolated antibody or antigen binding fragment thereof that binds human PD-L1 can comprise three of the light chain complementarity determining regions (CDRs) and three of the heavy chain CDRs shown in Tables 1 to 3 below.

TABLE 1

Characteristics of Monoclonal Antibody MEB037.20C3

| Antibody Feature | Amino Acid Sequence | SEQ ID NO |
|---|---|---|
| Light Chain | | |
| CDRL1 | KSSQSLLNSRTRKNYLA | 9 |
| CDRL2 | WASTRES | 2 |
| CDRL3 | QQSYDVVT | 10 |
| Leader Sequence | MDSQAQVLILLLLWVSGTFG | 11 |
| Variable Region | MDSQAQVLILLLLWVSGTFGDIVMSQSPSSLAVSAGEKVTMSCKSSQ SLLNSRTRKNYLAWYQQKPGQSPKLLIYWASTRESGVPDRFTGSGSG TDFTLTISSVQAEDLAVYYCQQSYDVVTFGAGTKLELK | 12 |
| Mature Variable Region | DIVMSQSPSSLAVSAGEKVTMSCKSSQSLLNSRTRKNYLAWYQQKPG QSPKLLIYWASTRESGVPDRFTGSGSGTDFTLTISSVQAEDLAVYYC QQSYDVVTFGAGTKLELK | 13 |
| DNA Sequence Encoding the Variable Region | ATGGATTCACAGGCCCAGGTTCTTATATTGCTGCTGCTATGGGTATC TGGTACCTTTGGGGACATTGTGATGTCACAATCTCCATCCTCCCTGG CTGTGTCAGCAGGAGAGAAGGTCACTATGAGCTGCAAATCCAGTCAG AGTCTGCTCAACAGTAGAACCCGAAAGAACTACTTGGCTTGGTACCA GCAGAAACCAGGGCAGTCTCCTAAACTGCTGATCTACTGGGCATCCA CTAGGGAATCTGGGGTCCCTGATCGCTTCACAGGCAGTGGATCTGGG ACAGATTTCACTCTCACCATCAGCAGTGTGCAGGCTGAAGACCTGGC AGTTTATTACTGCCAGCAATCTTATGATGTGGTCACGTTCGGTGCTG GGACCAAGCTGGAGCTGAAA | 33 |
| Heavy Chain | | |
| CDRH1 Kabat Def'n | SYWMH | 14 |
| CDRH1 Chothia Def'n | GYIFTSYWMH | 15 |
| CDRH2 | YINPSSDYNEYSEKFMD | 16 |
| CDRH3 | SGWLVHGDYYFDY | 17 |
| Leader Sequence | MERHWIFLFLFSVTAGVHS | 18 |
| Variable Region | MERHWIFLFLFSVTAGVHSQVQVQQSGAELAEPGASVKMSCKASGYI FTSYWMHWLKQRPGQGLEWIGYINPSSDYNEYSEKFMDKATLTADKA STTAYMQLISLTSEDSAVYYCARSGWLVHGDYYFDYWGQGTTLTVSS | 19 |

TABLE 1-continued

Characteristics of Monoclonal Antibody MEB037.20C3

| Antibody Feature | Amino Acid Sequence | SEQ ID NO |
| --- | --- | --- |
| Mature Variable Region | QVQVQQSGAELAEPGASVKMSCKASGYIFTSYWMHWLKQRPGQGLEW IGYINPSSDYNEYSEKFMDKATLTADKASTTAYMQLISLTSEDSAVY YCARSGWLVHGDYYFDYWGQGTTLTVSS | 20 |
| DNA Sequence Encoding Variable Region | ATGGAAAGGCACTGGATCTTTCTCTTCCTGTTTTCAGTAACTGCAGG TGTCCACTCCCAGGTCCAGGTTCAGCAGTCTGGGGCTGAACTGGCAG AACCTGGGGCCTCAGTGAAGATGTCCTGCAAGGCCTCTGGCTACATC TTTACTAGCTACTGGATGCACTGGCTAAAGCAGAGGCCTGGACAGGG TCTGGAATGGATTGGATACATTAATCCCAGCAGTGATTATAATGAAT ACAGTGAGAAATTCATGGACAAGGCCACATTGACTGCAGACAAAGCC TCCACCACAGCCTACATGCAACTGATCAGCCTGACATCTGAGGACTC TGCAGTCTATTACTGTGCAAGATCGGGATGGTTAGTACATGGAGACT ATTATTTTGACTACTGGGGCCAAGGCACCACTCTCACAGTCTCCTCA | 34 |

TABLE 2

Characteristics of Monoclonal Antibody MEB037.22C3

| Antibody Feature | Amino Acid Sequence | SEQ ID NO |
| --- | --- | --- |
| Light Chain | | |
| CDRL1 | KSSQSLLHTSTRKNYLA | 21 |
| CDRL2 | WASTRES | 2 |
| CDRL3 | KQSYDVVT | 22 |
| Leader Sequence | MDSQAQVLILLLLWVSGTCG | 23 |
| Variable Region | MDSQAQVLILLLLWVSGTCGDIVMSQSPSSLAVSAGEKVTMTCKSSQ SLLHTSTRKNYLAWYQQKPGQSPKLLIYWASTRESGVPDRFTGSGSG TDFTLTISSVQAEDLAVYYCKQSYDVVTFGAGTKLELK | 24 |
| Mature Variable Region | DIVMSQSPSSLAVSAGEKVTMTCKSSQSLLHTSTRKNYLAWYQQKPG QSPKLLIYWASTRESGVPDRFTGSGSGTDFTLTISSVQAEDLAVYYC KQSYDVVTFGAGTKLELK | 25 |
| DNA Sequence Encoding Variable Region | ATGGATTCACAGGCCCAGGTTCTTATATTGCTGCTGCTATGGGTATC TGGTACCTGTGGGGACATTGTGATGTCACAGTCTCCCTCCTCCCTGG CTGTGTCAGCAGGAGAGAAGGTCACTATGACCTGCAAATCCAGTCAG AGTCTGCTCCACACTAGCACCCGAAAGAACTACTTGGCTTGGTACCA GCAGAAACCAGGGCAGTCTCCTAAACTGCTGATCTATTGGGCATCCA CTAGGGAATCTGGGGTCCCTGATCGCTTCACAGGCAGTGGATCTGGG ACAGATTTCACTCTCACCATCAGCAGTGTGCAGGCTGAAGACCTGGC AGTTTATTACTGCAAACAATCTTATGATGTGGTCACGTTCGGTGCTG GGACCAAGCTGGAGCTGAAA | 35 |
| Heavy Chain | | |
| CDRH1 Kabat Def'n | SYWIH | 26 |
| CDRH1 Chothia Def'n | GTTFTSYWIH | 27 |
| CDRH2 | YINPSSGYHEYNQKFID | 28 |
| CDRH3 | SGWLIHGDYYFDF | 29 |
| Leader Sequence | MERHWIFLFLFSVTAGVHS | 30 |
| Variable Region | MERHWIFLFLFSVTAGVHSQVHLQQSGAELAKPGASVKMSCKASGYT FTSYWIHWIKQRPGQGLEWIGYINPSSGYHEYNQKFIDKATLTADRS SSTAYMHLTSLTSEDSAVYYCARSGWLIHGDYYFDFWGQGTTLTVSS | 31 |
| Mature Variable Region | XVHLQQSGAELAKPGASVKMSCKASGYTFTSYWIHWIKQRPGQGLEW IGYINPSSGYHEYNQKFIDKATLTADRSSSTAYMHLTSLTSEDSAVY YCARSGWLIHGDYYFDFWGQGTTLTVSS, wherein X = Q or pE | |
| DNA Sequence Encoding Variable Region | ATGGAAAGGCACTGGATCTTTCTCTTCCTGTTTTCAGTAACTGCAGG TGTCCACTCCCAGGTCCACCTTCAGCAGTCTGGGGCTGAACTGGCAA AACCTGGGGCCTCAGTGAAGATGTCCTGCAAGGCTTCTGGCTACACG TTTACTAGTTACTGGATACACTGGATAAAGCAGAGGCCTGGACAGGG TCTGGAATGGATTGGATACATTAATCCTTCCTCTGGTTATCATGAAT ACAATCAGAAATTCATTGACAAGGCCACATTGACTGCTGACAGATCC TCCAGCACAGCCTACATGCACCTGACCAGCCTGACGTCTGAAGACTC TGCAGTCTATTACTGTGCAAGATCGGGATGGTTAATACATGGAGACT ACTACTTTGACTTCTGGGGCCAAGGCACCACTCTCACAGTCTCCTCA | 36 |

TABLE 3

Consensus Antibody Sequences of the Invention

| Antibody Feature | Amino Acid Sequence | SEQ ID NO |
|---|---|---|
| | Light Chain | |
| CDRL1 | KSSQSLLX$_1$X$_2$X$_3$TRKNYLA, wherein X$_1$ = H or N, X$_2$ = S or T, and X$_3$ = R or S | 1 |
| CDRL2 | WASTRES | 2 |
| CDRL3 | X$_1$QSYDVVT, wherein X$_1$ = Q or K | 3 |
| Mature Variable Region | DIVMSQSPSSLAVSAGEKVTMX$_1$CKSSQSLL X$_2$X$_3$X$_4$TRKNYLAWYQQKPGQSPKLLIYWASTRESGVPDRFTGSGSGTDF TLTISSVQAEDLAVYYCX$_5$QSYDVVTFGAGTKLELK, wherein X$_1$ = S or T, X$_2$ = H or N, X$_3$ = S or T, X$_4$ = R or S, and X$_5$ = Q or K | 4 |
| | Heavy Chain | |
| CDRH1 | SYWXH, wherein X = I or M | 5 |
| CDRH2 | YINPSSX$_1$YX$_2$EYX$_3$X$_4$KFX$_5$D, wherein X$_1$ = D or G, X$_2$ = H or N X$_3$ = S or N, X$_4$ = E or Q, and X$_5$ = I or M | 6 |
| CDRH3 | SGWLX$_1$HGDYYFDX$_2$, wherein X$_1$ = I or V and X$_2$ = F or Y | 7 |
| Mature Variable Region | XVX$_1$X$_2$QQSGAELAX$_3$PGASVKMSCKASGYIFTSYWX$_4$HWX$_5$KQRPGQGLE WIGYINPSSX$_6$YX$_7$EYX$_8$X$_9$KFX$_{10}$DKATLTADX$_{11}$X$_{12}$SX$_{13}$TAYMX$_{14}$LX$_{15}$S LTSEDSAVYYCARSGWLX$_{16}$HGDYYFDX$_{17}$WGQGTTLTVSS, wherein X = Q or pE, X$_1$ = H or Q, X$_2$ = L or V, X$_3$ = E or K, X$_4$ = I or M, X$_5$ = I or L, X$_6$ = D or G, X$_7$ = H or N, X$_8$ = N or S, X$_9$ = E or Q, X$_{10}$ = I or M, X$_{11}$ = K or R, X$_{12}$ = A or S, X$_{13}$ = S or T, X$_{14}$ = H or Qf X$_{15}$ = I or T, X$_{16}$ = I or V, and X$_{17}$ = F or Y | 8 |

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 4.

TABLE 4

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |

TABLE 4-continued

Exemplary Conservative Amino Acid Substitutions

| Original residue | Conservative substitution |
|---|---|
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such an antigen affinity and/or specificity. Such variants include, but are not limited to, replacement of an amino acid with one having similar properties, such as the conservative amino acid substitutions of Table 4.

In another embodiment, the invention includes an antibody or antigen binding fragment thereof that specifically binds PD-L1 and has $V_L$ domains and $V_H$ domains and shares 100% sequence homology to the light and heavy chain CDRs of Tables 1 or 2, and at least 90%, 92%, 94%, 96%, 98% or 99% sequence homology to the light and heavy chain mature variable regions of Tables 1 or 2.

Nucleic Acids

The present invention also provides nucleic acids encoding the immunoglobulin chains of anti-PD-L1 antibodies and antigen binding fragments disclosed herein. For example, the present invention includes nucleic acids encoding the amino acids described in Tables 1, 2 and 3, as well as nucleic acids which hybridize thereto.

In general, the nucleic acids hybridize under low, moderate or high stringency conditions, and encode antibodies that maintain the ability to specifically bind to PD-L1. A first nucleic acid molecule is "hybridizable" to a second nucleic acid molecule when a single stranded form of the first nucleic acid molecule can anneal to the second nucleic acid molecule under the appropriate conditions of temperature and solution ionic strength (see Sambrook, et al., supra). The conditions of temperature and ionic strength determine the "stringency" of the hybridization. Typical low stringency hybridization conditions include 55° C., 5×SSC, 0.1% SDS and no formamide; or 30% formamide, 5×SSC, 0.5% SDS at 42° C. Typical moderate stringency hybridization conditions are 40% formamide, with 5× or 6×SSC and 0.1% SDS at 42° C. High stringency hybridization conditions are 50% formamide, 5× or 6×SSC at 42° C. or, optionally, at a higher temperature (e.g., 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, e.g., oligonucleotides, the position of mismatches becomes more important, and the length of the oligonucleotide determines its specificity (see Sambrook, et al., supra, 11.7-11.8).

The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

In another embodiment, the invention provides an isolated nucleic acid or nucleic acids, for example DNA, encoding at least one of the polypeptide chains of the isolated anti-PD-L1 antibodies or antigen binding fragments described herein. In some embodiments the isolated nucleic acid encodes both a light chain and a heavy chain on a single nucleic acid molecule, and in other embodiments the light and heavy chains are encoded on separate nucleic acid molecules. In another embodiment the nucleic acids further encodes a signal sequence.

The present invention also provides expression vectors comprising the isolated nucleic acids of the invention, wherein the nucleic acid is operably linked to control sequences that are recognized by a host cell when the host cell is transfected with the vector. Also provided are host cells comprising an expression vector of the present invention and methods for producing the antibody or antigen binding fragment thereof disclosed herein comprising culturing a host cell harboring an expression vector encoding the antibody or antigen binding fragment in culture medium, and isolating the antigen or antigen binding fragment thereof from the host cell or culture medium.

Epitope Binding

The present invention further provides antibodies or antigen binding fragments thereof that block binding of antibody 20C3 or 22C3 to human PD-L1 by binding to the same epitope as 20C3 or 22C3, respectively. Such antibodies and binding fragments may be identified using any cross-blocking or competition analysis known in the art, including the Octet competition analyses described in Example 2, followed by identifying the epitope on human PD-L1 to which the cross-blocking antibody binds. A first antibody is considered to cross-block binding of a second antibody if prebinding the target with the first antibody to saturation increases the concentration of second antibody needed to achieve half-maximal binding of the target by 2-, 3-, 4-, 5-, 10-, 20-, 50-, 100-, 200-fold or more. The binding epitope for a cross-blocking antibody can be identified using techniques well-known in the art.

One such epitope mapping technique is hydrogen/deuterium exchange coupled with proteolysis and mass spectrometry (HDX-MS). This method relies on the accurate measurement and comparison of the degree of deuterium incorporation by an antigen when incubated in heavy water ($D_2O$) on its own and in the presence of its antibody at various time intervals. Deuterium is exchanged with hydrogen on the amide backbone of the proteins in exposed areas whereas regions of the antigen bound to the antibody will be protected and will show less or no exchange after analysis by liquid chromatography-tandem mass spectrometry (LC-MS/MS) of proteolytic fragments.

Based on the HDX-MS epitope mapping described in Example 3, the proposed epitope on mature human PD-L1 for antibody 22C3 comprises residues in two discontinuous amino acid segments in the extracellular domain (SEQ ID NO:38): 156 to 178 and 196 to 206. Additional epitope residues are likely present in the following segments in the extracellular domain (SEQ ID NO:38): 3 to 9; 10 to 13; 88 to 93 and 135 to 147.

Thus, in one embodiment, an antibody that blocks binding of antibody 22C3 to human PD-L1 by binding to the same epitope as 22C3 binds to residues in a first segment of amino acids 156 to 178 of SEQ ID NO:38 and to residues in a second segment of amino acids 196 to 206 of SEQ ID NO:38, and in some embodiments also binds to residues in any one, two, or three, or in all four, of the following segments of SEQ ID NO:38: amino acids 3 to 9; amino acids 10 to 13; amino acids 88 to 93 and amino acids 135 to 147.

Methods of Making Antibodies and Antigen Binding Fragments Thereof

Hybridoma cells that produce parental (e.g. rodent) monoclonal anti-X antibodies may be produced by methods which are commonly known in the art. These methods include, but are not limited to, the hybridoma technique originally developed by Kohler, et al., (1975) (Nature 256:495-497), as well as the trioma technique (Hering, et al., (1988) Biomed. Biochim. Acta. 47:211-216 and Hagiwara, et al., (1993) Hum. Antibod. Hybridomas 4:15), the human B-cell hybridoma technique (Kozbor, et al., (1983) Immunology Today 4:72 and Cote, et al., (1983) Proc. Natl. Acad. Sci. U.S.A 80:2026-2030), the EBV-hybridoma technique (Cole, et al., in *Monoclonal Antibodies and Cancer Therapy*, Alan R. Liss, Inc., pp. 77-96, 1985), and electric field based electrofusion using a Cyto Pulse large chamber cull fusion electroporator (Cyto Pulse Sciences, Inc., Glen Burnie, Md.). Preferably, mouse splenocytes are isolated and fused with PEG or by electrofusion to a mouse myeloma cell line based upon standard protocols.

The resulting hybridomas may then be screened for the production of antigen-specific antibodies. For example, single cell suspensions of splenic lymphocytes from immunized mice may by fused to one-sixth the number of P3X63-Ag8.653 nonsecreting mouse myeloma cells (ATCC, CRL 1580) with 50% PEG. Cells may be plated at approximately $2 \times 10^5$ cells/mL in a flat bottom microtiter plate, followed by a two week incubation in selective medium containing 20% fetal Clone Serum, 18% "653" conditioned media, 5% origen (IGEN), 4 mM L-glutamine, 1 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1× HAT (Sigma; the HAT is added 24 hours after the fusion). After two weeks, cells may be cultured in medium in which the HAT is replaced with HT. Individual wells may then be screened by ELISA for anti-X monoclonal IgG antibodies. Once extensive hybridoma growth occurs, medium can be observed usually after 10-14 days. The antibody secreting hybridomas may be replated, screened again, and if still positive for human IgG, anti-X monoclonal antibodies, can be subcloned at least twice by limiting dilution.

The stable subclones may then be cultured in vitro to generate small amounts of antibody in tissue culture medium for characterization. For example, about 1 gram of the 22C3 antibody may be produced and purified from the mouse hybridoma cell line MEB037.22C3.138 using the following procedure. Frozen MEB037.22C3.138 cells are thawed into are adapted into shake flask using hybridoma serum free media with 2 mM additional L-glutamine with or without 0.18% Pluronic F-68. The presence of Pluronic F-68 may improve the viability of the shake flask culture. Once the cells are completely adapted into shake flask, a 20 liter production culture is performed in serum free media in a WAVE bioreactor (GE Healthcare Life Sciences) with the addition of 10% CHO CD efficient Feed B (Invitrogen, Catalogue #A10240-01). For cell expansion, a 1 liter culture is initiated in a small WAVE bag, and then the 1 L WAVE culture is expanded into a 20 L culture in the WAVE bioreactor. The 20 liter culture may be initiated at a cell density of $0.5 \times 10^6$ viable cells/mL, fed with 10% CHO CD Efficient Feed B on Day 1, and pH adjusted daily with 1N $Na_2CO_3$. The cells are harvested after four days. Small samples may be collected daily for NOVA analysis.

Anti-hPD-L1 antibodies of the invention may be purified from a hybridoma culture by the following process. The hybridoma culture is clarified by depth filtration using 1.2 micrometer glass fiber and 0.2 micrometer cellulose acetate filter. An equal volume of 2× ProSepA Buffer (100 mM Boric Acid, 5M NaCl, pH 8.5) is added to the clarified harvest and the diluted harvest is loaded onto a 170 mL bed volume Protein-A column. The column is washed with 5 column volumes (CV) of 1× ProSepA Buffer (50 mM Boric Acid, 2.5M NaCl, pH 8.5), then washed with 2CV of 1×PBS, and the anti-hPD-L1 antibody eluted with 5CV of Elution Buffer (0.1M Glycine, pH 3.0). The elution fractions containing IgG are combined and the pH neutralized by adding ⅒th volume of 1.0M Tris, pH buffer. The neutralized antibody composition is then sterile filtered using a 10 kDa disposable TFF cassette. The antibody may be formulated for storage by diafiltration against 10 liter of formulation buffer (20 mM sodium acetate, 9% sucrose, pH 5.0) and using 20 volume changes. Using this protocol, antibody 22C3 at a concentration of about 5.0 mg/ml can be prepared and having a purity of at least 98% by SDS-PAGE, SEC HPLC and C8 RP-HPLC measurements, with endotoxin levels of less than 0.1 EU/ml and less than 0.02 EU/mg.

The anti-PD-L1 antibodies disclosed herein may also be produced recombinantly (e.g., in an *E. coli*/T7 expression system as discussed above). In this embodiment, nucleic acids encoding the antibody molecules of the invention (e.g., $V_H$ or $V_L$) may be inserted into a pET-based plasmid and expressed in the *E. coli*/T7 system. There are several methods by which to produce recombinant antibodies which are known in the art. One example of a method for recombinant production of antibodies is disclosed in U.S. Pat. No. 4,816,567. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

Anti-PD-L1 antibodies can also be synthesized by any of the methods set forth in U.S. Pat. No. 6,331,415.

Mammalian cell lines available as hosts for expression of the antibodies or fragments disclosed herein are well known in the art and include many immortalized cell lines available from the American Type Culture Collection (ATCC). These include, inter alia, Chinese hamster ovary (CHO) cells, NS0, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

A polyclonal antibody is an antibody which was produced among or in the presence of one or more other, non-identical antibodies. In general, polyclonal antibodies are produced from collections of different B-lymphocytes, e.g. the B-lymphocyte of an animal treated with an immunogen of interest, which produces a population of different antibodies that are all directed to the immunogen. Usually, polyclonal antibodies are obtained directly from an immunized animal, e.g. spleen, serum or ascites fluid.

The present invention further includes antibody fragments of the anti-PD-L1 antibodies disclosed herein. The antibody fragments include F(ab)$_2$ fragments, which may be produced by enzymatic cleavage of an IgG by, for example, pepsin. Fab fragments may be produced by, for example, reduction of F(ab)$_2$ with dithiothreitol or mercaptoethylamine. A Fab fragment is a $V_L$-$C_L$ chain appended to a $V_H$-$C_{H1}$ chain by a disulfide bridge. A F(ab)$_2$ fragment is two Fab fragments which, in turn, are appended by two disulfide bridges. The Fab portion of an F(ab)$_2$ molecule includes a portion of the $F_c$ region between which disulfide bridges are located. An $F_v$ fragment is a $V_L$ or $V_H$ region.

Immunoglobulins may be assigned to different classes depending on the amino acid sequences of the constant domain of their heavy chains. There are at least five major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The invention comprises antibodies and antigen binding fragments of any of these classes or subclasses of antibodies.

In one embodiment, the antibody or antigen binding fragment comprises a heavy chain constant region, e.g. a human constant region, such as γ1, γ2, γ3, or γ4 human heavy chain constant region or a variant thereof. In another embodiment, the antibody or antigen binding fragment comprises a light chain constant region, e.g. a human light chain constant region, such as lambda or kappa human light chain region or variant thereof. By way of example, and not limitation the human heavy chain constant region can be γ1 and the human light chain constant region can be kappa. In an alternative embodiment, the Fc region of the antibody is γ4 with a Ser228Pro mutation (Schuurman, J et. al., *Mol. Immunol.* 38: 1-8, 2001).

In some embodiments, different constant domains may be appended to humanized $V_L$ and $V_H$ regions derived from the CDRs provided herein. For example, if a particular intended use of an antibody (or fragment) of the present invention were to call for altered effector functions, a heavy chain constant domain other than human IgG1 may be used, or hybrid IgG1/IgG4 may be utilized.

Antibody Engineering

In particular embodiments, it will be desirable to change certain amino acids containing exposed side-chains to another amino acid residue in order to provide for greater chemical stability of the final antibody, as follows. The deamidation of asparagine may occur on N-G or D-G sequences and result in the creation of an isoaspartic acid residue that introduces a kink into the polypeptide chain and decreases its stability (isoaspartic acid effect). In certain embodiments, the antibodies of the present disclosure do not contain asparagine isomerism sites.

For example, an asparagine (Asn) residue may be changed to Gln or Ala to reduce the potential for formation of isoaspartate at any Asn-Gly sequences, particularly within a CDR. A similar problem may occur at a Asp-Gly sequence. Reissner and Aswad (2003) *Cell. Mol. Life Sci.* 60:1281. Isoaspartate formation may debilitate or completely abrogate binding of an antibody to its target antigen. See, Presta (2005) *J. Allergy Clin. Immunol.* 116:731 at 734. In one embodiment, the asparagine is changed to glutamine (Gln). It may also be desirable to alter an amino acid adjacent to an asparagine (Asn) or glutamine (Gln) residue to reduce the likelihood of deamidation, which occurs at greater rates when small amino acids occur adjacent to asparagine or glutamine. See, Bischoff & Kolbe (1994) *J. Chromatog.* 662:261. In addition, any methionine residues (typically solvent exposed Met) in CDRs may be changed to Lys, Leu, Ala, or Phe in order to reduce the possibility that the methionine sulfur would oxidize, which could reduce antigen binding affinity and also contribute to molecular heterogeneity in the final antibody preparation. Id. In one embodiment, the methionine is changed to alanine (Ala). Additionally, in order to prevent or minimize potential scissile Asn-Pro peptide bonds, it may be desirable to alter any Asn-Pro combinations found in a CDR to Gln-Pro, Ala-Pro, or Asn-Ala. Antibodies with such substitutions are subsequently screened to ensure that the substitutions do not decrease the affinity or specificity of the antibody for human PD-L1, or other desired biological activity to unacceptable levels.

TABLE 5

Exemplary stabilizing CDR variants

| CDR Residue | Stabilizing Variant Sequence |
|---|---|
| Asn—Gly | Gln—Gly, Ala—Gly, or Asn—Ala |
| (N—G) | (Q—G), (A—G), or (N—A) |
| Asp—Gly | Glu—Gly, Ala—Gly or Asp—Ala |
| (D—G) | (E—G), (A—G), or (D—A) |
| Met (typically solvent exposed) | Lys, Leu, Ala, or Phe |
| (M) | (K), (L), (A), or (F) |
| Asn | Gln or Ala |
| (N) | (Q) or (A) |
| Asn—Pro | Gln—Pro, Ala—Pro, or Asn—Ala |
| (N—P) | (Q—P), (A—P), or (N—A) |

Antibody Conjugates

The anti-PD-L1 antibody molecules disclosed herein may also be conjugated to a chemical moiety such as a radionuclide or other detectable label. Radionuclides include $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$Cu, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr, and $^{56}$Fe. Fluorescent or chemilluminescent labels include fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

Any method known in the art for conjugating the antibody molecules to the various moieties may be employed, including those methods described by Hunter, et al., (1962) *Nature* 144:945; David, et al., (1974) *Biochemistry* 13:1014; Pain, et al., (1981) J. Immunol. Meth. 40:219; and Nygren, J., (1982) *Histochem. and Cytochem.* 30:407. Methods for conjugating antibodies are conventional and very well known in the art.

Experimental and Diagnostic Uses

The anti-PD-L1 antibodies and antibody fragments disclosed herein may be used to specifically detect human PD-L1 expressed on the surface of a cell. The cell may be present in a tissue or serum sample obtained from a human individual and the detection of PD-L1 expression is performed using any of a variety of in vitro assay methods known in the art.

For example, particular embodiments include ELISA assays (enzyme-linked immunosorbent assay), which typically comprises the following steps:

(a) coat a substrate (e.g., surface of a microtiter plate well, e.g., a plastic plate) with an anti-PD-L1 antibody antigen-binding fragment thereof;

(b) apply a sample to be tested for the presence of human PD-L1 to the substrate;

(c) wash the plate, so that unbound material in the sample is removed;

(d) apply detectably labeled antibodies (e.g., enzyme-linked antibodies) which are also specific to human PD-L1;

(e) wash the substrate, so that the unbound, labeled antibodies are removed;

(f) if the labeled antibodies are enzyme linked, apply a chemical which is converted by the enzyme into a fluorescent signal; and (g) detect the presence of the labeled antibody.

In a further embodiment, the labeled antibody is labeled with peroxidase which reacts with ABTS (e.g., 2,2'-azino-bis(3-ethylbenzthiazoline-6-sulphonic acid)) or 3,3',5,5'-Tetramethylbenzidine to produce a color change which is detectable. Alternatively, the labeled antibody is labeled with a detectable radioisotope (e.g., $^3$H) which can be detected by scintillation counter in the presence of a scintillant.

Anti-PD-L1 antibodies and antigen binding fragments thereof of the invention may be used in a Western blot or immunoprotein blot procedure. Such a procedure forms part of the present invention and includes e.g.:

(1) contacting a membrane or other solid substrate to be tested for the presence of human PD-L1 thereof with an antibody or antigen-binding fragment thereof of the invention. Such a membrane may take the form of a nitrocellulose or vinyl-based (e.g., polyvinylidene fluoride (PVDF)) membrane to which proteins to be tested for the presence of X in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contact of membrane with the anti-PD-L1 antibody or fragment, the membrane is optionally blocked, e.g., with non-fat dry milk or the like so as to bind non-specific protein binding sites on the membrane (2) washing the membrane one or more times to remove unbound anti-PD-L1 antibody or fragment and other unbound substances; and (3) detecting the bound anti-PD-L1 antibody or fragment. The bound antibody or fragment may be detected by incubating the bound antibody or fragment with a secondary antibody (an anti-immunoglobulin antibody) which is detectably labeled and, then, detecting the presence of the secondary antibody.

The anti-PD-L1 antibodies and antigen-binding fragments thereof disclosed herein may also be used in immunohistochemistry (IHC) assays, which may be performed using a variety of IHC formats known in the art, and constitute embodiments of the invention. A typical IHC assay uses an FFPE tissue section of about 3-4 millimeters, and preferably 4 micrometers, mounted and dried on a microscope slide and comprises, e.g., (1) subjecting the tissue section to deparaffinization and hydration, contacting the rehydrated tissue section with an anti-PD-L1 antibody or antigen-binding fragment thereof of the invention; and (2) detecting the anti-PD-L1 antibody or antigen-binding fragment thereof on the surface of one or more cells in the tissue. If the antibody or fragment itself is detectably labeled, it can be detected directly. Alternatively, the antibody or fragment may be bound by a detectably labeled secondary antibody which is detected.

A preferred IHC assay employs the commercially available Dako EnVision™ FLEX detection system, which is intended for use together with a Dako Autostainer instrument (Dako, an Agilent Technologies Company, Glostrup, Denmark). When employing this system with the 22C3 antibody, or an antibody that comprises the heavy and light chain variable regions of the 22C3 antibody, the IHC assay may be performed as follows. Four micron thick FFPE sections of tissue mounted on slides are air-dried overnight, baked at 60° C. for 45 minutes, deparaffinized, and rehydrated. After deparaffinization, FFPE slides are subjected to heat-induced epitope retrieval using EnVision™ FLEX High pH Target Retrieval Solution at 97° C. followed by 20 minutes at room temp. The slides are then washed, stained with 22C3 at 2 µg/mL for 60 minutes, and then detected using Dako EnVision™ FLEX reagents as follows: EnVision™ FLEX+MS Linker (15 minutes), EnVision™ FLEX/HRP (20 minutes), EnVision™ FLEX DAB (10 minutes), and DAB Enhancer (7 minutes) with intervening wash steps.

Certain anti-PD-L1 antibodies and antigen-binding fragments thereof disclosed herein may also be used for in vivo tumor imaging. Such a method may include injection of a radiolabeled anti-PD-L1 antibody or antigen-binding fragment thereof into the body of a human patient to be tested for the presence of a tumor associated with PD-L1 expression followed by nuclear imaging of the body of the patient to detect the presence of the labeled antibody or fragment e.g., at loci comprising a high concentration of the antibody or fragment which are bound to the tumor.

Imaging techniques include SPECT imaging (single photon emission computed tomography) or PET imaging (positron emission tomography). Labels include e.g., iodine-123 ($^{123}$I) and technetium-99m ($^{99m}$Tc), e.g., in conjunction with SPECT imaging or $^{11}$C, $^{13}$N, $^{15}$O or $^{18}$F, e.g., in conjunction with PET imaging or Indium-111 (See e.g., Gordon et al., (2005) International Rev. Neurobiol. 67:385-440).

Detection Kits and Therapeutic Kits

As a matter of convenience, an antibody or specific binding agent disclosed herein can be provided in a kit, i.e., a packaged combination of reagents in predetermined amounts with instructions for performing the diagnostic or detection assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Also provided are diagnostic or detection reagents and kits comprising one or more such reagents for use in a variety of detection assays, including for example, immunoassays such as ELISA (sandwich-type or competitive format). The kit's components may be pre-attached to a solid support, or may be applied to the surface of a solid support when the kit is used. In some embodiments, the signal generating means may come pre-associated with an antibody of the invention or may require combination with one or more components, e.g., buffers, antibody-enzyme conjugates, enzyme substrates, or the like, prior to use. Kits may also include additional reagents, e.g., blocking reagents for reducing nonspecific binding to the solid phase surface, washing reagents, enzyme substrates, and the like. The solid phase surface may be in the form of a tube, a bead, a microtiter plate, a microsphere, or other materials suitable for immobilizing proteins, peptides, or polypeptides. In particular aspects, an enzyme that catalyzes the formation of a chemiluminescent or chromogenic product or the reduction of a chemiluminescent or chromogenic substrate is a component of the signal generating means. Such enzymes are well known in the art. Kits may comprise any of the capture agents and detection reagents described herein. Optionally the kit may also comprise instructions for carrying out the methods of the invention.

The detection kits disclosed herein may also be prepared that comprise at least one of the antibody or antigen-binding fragment disclosed herein and instructions for using the composition as a detection reagent. Containers for use in such kits may typically comprise at least one vial, test tube, flask, bottle, syringe or other suitable container, into which one or more of the detection composition(s) may be placed, and preferably suitably aliquoted. The kits disclosed herein will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent may be provided either in the same container as the detection composition itself, or may alternatively be placed in a second distinct container means into which this second composition may be placed and suitably aliquoted. Alternatively, the detection reagent may be prepared in a single container means, and in most cases, the kit will also typically include a means for containing the vial(s) in close confinement for commercial sale and/or convenient packaging and delivery.

A device or apparatus for carrying out the detection or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

Further embodiments also provide a processor, a computer readable memory, and a routine stored on the computer readable memory and adapted to be executed on the processor to perform any of the methods described herein. Examples of suitable computing systems, environments, and/or configurations include personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, or any other systems known in the art.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning, $3^{rd}$* ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology, Vols.* 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, N.Y.; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) *J. Biol. Chem.* 274:27371-27378; Baca et al. (1997) *J. Biol. Chem.* 272: 10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature Biotechnol.* 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol.* 17:397-399).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry, 2nd ed.*; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

EXAMPLES

Example 1

Generation and Screening of Anti-PD-L1 Hybridomas

Balb/C mice were immunized with a human PD-L1-Fc fusion protein (R&D Systems® Catalogue No. 156-B7-100) in adjuvant. This fusion protein contains the extracellular domain of PD-L1 (Phe19-Thr239) fused to a human IgG1 fragment (Pro100-Lys 300). After 12 immunizations, lymph nodes from two mice with high titers to human PD-L1 were harvested and an electrofusion was performed to generate two batches of hybridomas, which were given the lab designations of MEB033 and MEB037.

Supernatants of the MEB033 and MEB037 hybridoma batches were screened to identify hybridomas that produce antibodies to human PD-L1. The screen employed a protein based ELISA for binding to the human hPD-L1-Fc protein; and cell based ELISAs for binding to human PD-L1-CHO human PD-L1-CHO stable transformants and parental CHO cells as a negative control. Supernatants from 88 clones of the MEB037 and from 23 clones of the MEB033 hybridoma tested positive for the presence of anti-PD-L1 antibody (data not shown) and samples thereof were tested for IHC reactivity on FFPE tissue sections from normal human tonsils (data not shown).

Of the 88 clones, only 11 clones from the MEB037 batch produced staining patterns of sufficient intensity and apparent specificity to warrant further evaluation, based on comparison with the staining patterns obtained with the commercially available anti-PD-L1 antibodies listed in the Table below:

TABLE 6

Commercially Available Anti-human PD-L1 Antibodies

| Company | Catalog Number | Species | Lot Number |
| --- | --- | --- | --- |
| eBioscience | 14-5983 | Mouse | 14-5983-82 |
| R&D | AF156 | Goat | EE1010109111 |
| US Biological | 22 | | |
| US Biological | 22E | | |
| Sigma | PRS4059 | Rabbit | 40590604 |

When the inventors compared the various staining patterns obtained with the experimental antibodies with patterns obtained with these commercially available anti-human PD-L1 antibodies, they observed significant differences between the staining patterns, including the localization of stain and the types of cells stained. In an attempt to explain these difference, the inventors conducted a number of additional experiments and discovered that none of these commercially available antibodies provided the combination of attributes required for use in IHC of PD-L1 expression in FFPE sections: (1) sensitivity—the ability to detect normal physiologic expression in positive control tissues (e.g., human tonsil) as well as expression in tumor tissue (e.g., human melanoma samples); (2) specificity—the staining pattern needs to correlate with known anatomic/cellular distribution of PD-L1 and needs to be neutralizable; and (3) robust—little to no variation in staining patterns when used to assay "duplicate" tissue sections.

For example, the inventors found that the Sigma/ProSco PRS4059 antibody showed multiple bands on tonsil lysate, none of which could be confirmed to represent PD-L1, failed to stain LOX melanoma cell lines that had been shown to be PD-L1 positive by flow cytometry, and failed to differentiate between positive and negative cell lines by IHC.

Figure 4B:
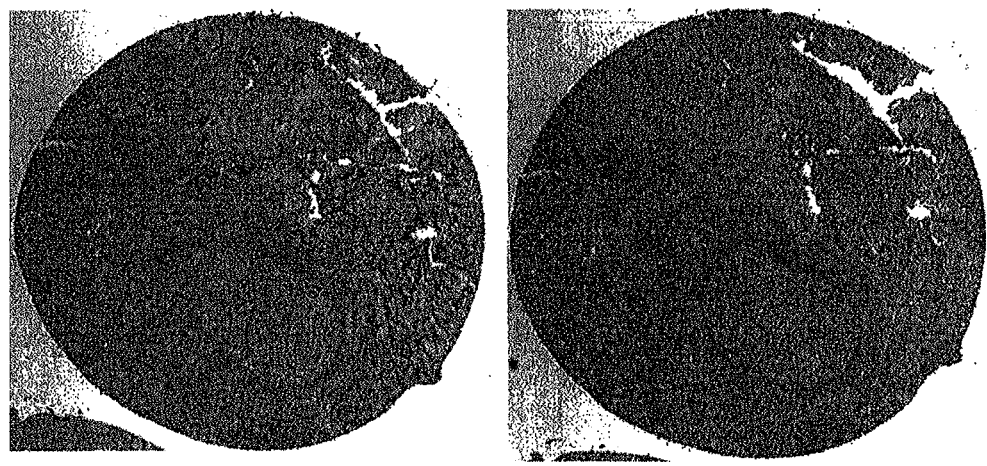

Some of these data are shown in FIG. 4, in which immunohistochemical staining of tonsil sections identified 22C3 and 20C3 as two antibodies with unusual and useful immunohistochemical properties on FFPE tissue as compared to the PRS4059 antibody identified by Gadiot et al (supra) as the only suitable candidate amongst 15 anti-human PD-L1 antibodies for detecting PD-L1 expression in FFPE tissue sections. In experiments performed by the inventors, the Prosci antibody (PRS4059, lot 40590604, used at 0.4 mg/ml primary, followed by the rabbit polymer detection system (DAKO Envision) stained all of the hematopoeitic lineages in the tonsil with equal intensity (FIG. 4A) whereas the 22C3 antibody selectively stained tonsil crypt epithelium and follicular CD68+ myeloid cells, which are morphologically consistent with macrophages (FIG. 4B). Substantially the same staining pattern was observed with antibody 20C3 (data not shown). Moreover, 22C3 and 20C3 demonstrate a consistent staining intensity difference between these two discrete cell populations with crypt epithelium much greater than follicular macrophages. All three antibodies could be neutralized by pre-incubation with the PD-L1 antigen, indicating that the reactivity is mediated by the antigen-binding domain (CDRs).

Example 2

Quality Assessment of the 20C3 and 22C3 Anti-PD-L1 Antibodies

This example describes additional experiments that were conducted to assess the utility of the 20C3 and 22C3 antibodies for use in IHC assays of FFPE tissue sections.

Figure 5A:
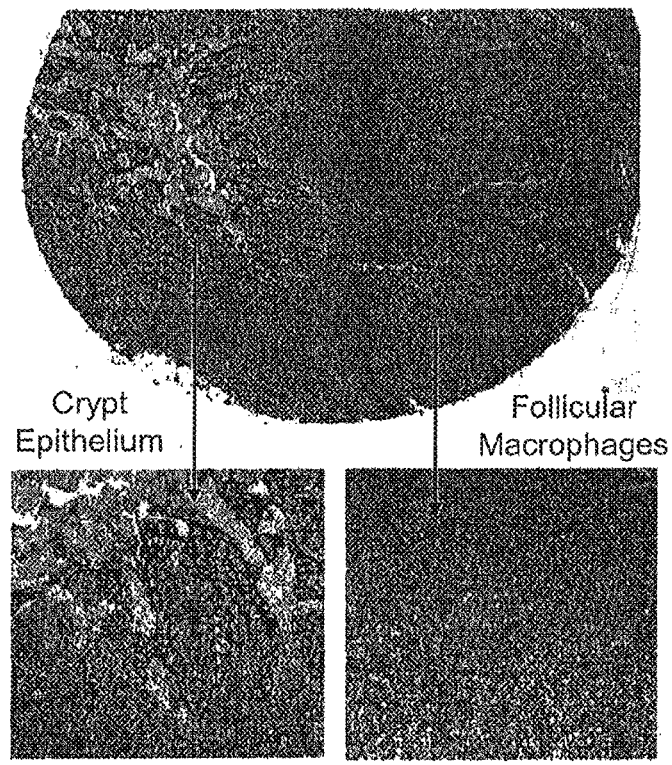
FIG. 5 shows photographs of adjacent normal FFPE tonsil tissue sections in which human PD-L1 protein and in-situ hybridization (ISH) mRNA expression was assayed by IHC assay using antibody 22C33 (FIG. 5A) and in-situ hybridization (ISH) (FIG. 5B), respectively, and which demonstrate differential staining between two unique cell populations: crypt epithelium (FIG. 5A, left enlarged view and FIG. 5B, top view) and follicular macrophages (FIG. 5A, right enlarged view and FIG. 5B, bottom view).
Figure 5B:
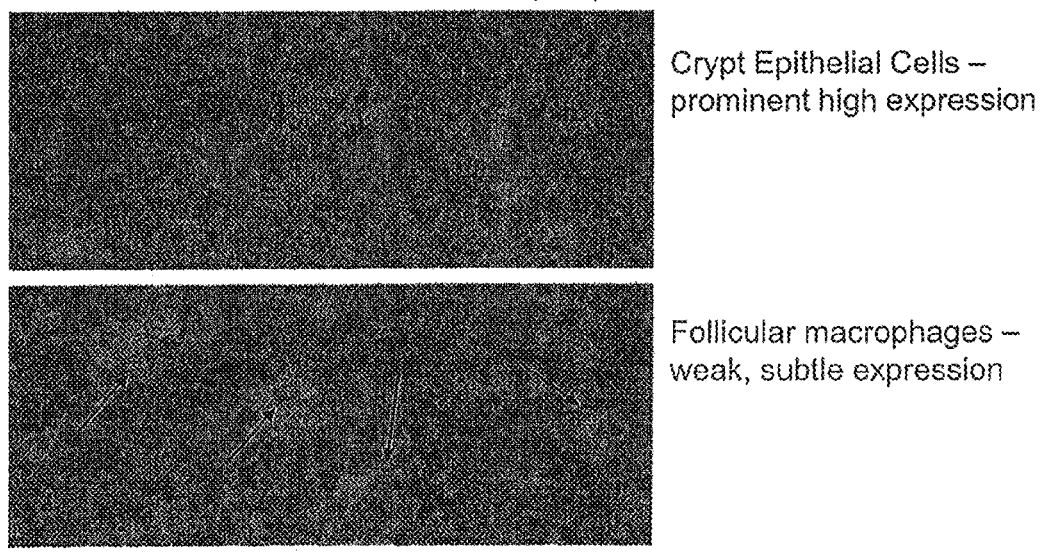

One experiment assessed the ability of these two antibodies to detect a range of human PD-L1 (hPD-L1) protein expression in IHC assay of normal human FFPE tonsil sections, and representative images for 22C3 are shown in FIG. 5A. Immunohistochemical staining with 22C3 labels tonsil crypt epithelium strongly as well as demonstrating weak-to-moderate staining of a CD68+ follicular myeloid population (presumed macrophages). Both antibodies (20C3 data not shown) label cells in a well-defined membranous/cell surface pattern in these two cell types. The appropriateness of hPD-L1 expression in tonsil (i.e. restriction of IHC staining to the two cell populations (crypt epithelium and follicular macrophages) was corroborated by an independent methodology (in-situ hybridization [ISH] for hPD-L1 mRNA) on adjacent FFPE tonsil tissue sections. In addition, the differential expression of hPD-L1 protein as assessed by IHC (crypt epithelium>>follicular macrophages) corresponds with the relative abundance of hPD-L1 mRNA observed with ISH.

Another experiment assessed the binding specificity of 20C3 and 22C3 for hPD-L1-expressing cells. HT144 cells which were known to be negative for expression of hPD-L1 by mRNA analysis (qPCR) and LOX melanoma cells known to express high levels of hPD-L1 mRNA (qPCR) were stained with 1 microgram/ml of purified mouse IgG from seven hybridomas generated in the experiments described in Example 1 above. An irrelevant isotype control mouse antibody was also used at the identical concentration. A fluorescent-labeled anti-mouse secondary antibody was used to detect the primary mouse antibodies. After staining and repeated washing, the cells were analyzed by flow cytometry, with median fluorescent intensities calculated for the population (>10,000 events collected). The results are shown in FIG. 6.

Figures 6A, 6B:
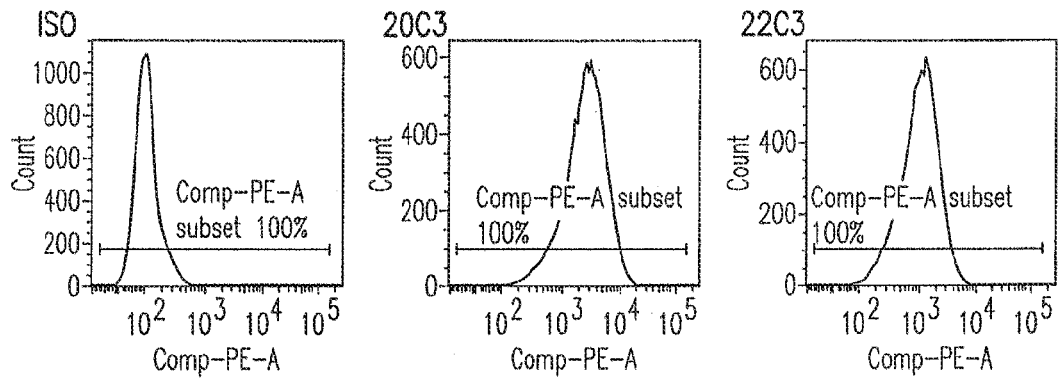
FIG. 6 illustrates the results of a flow cytometric assessment of the binding of various anti-human PD-L1 antibodies and an isotype control antibody to HT144 cells, which were known to be negative for expression of hPD-L1 by mRNA analysis (qPCR) (FIG. 6A) and LOX melanoma cells, which were known to express high levels of hPD-L1 mRNA (qPCR) (FIG. 6B).
Figure 8A:
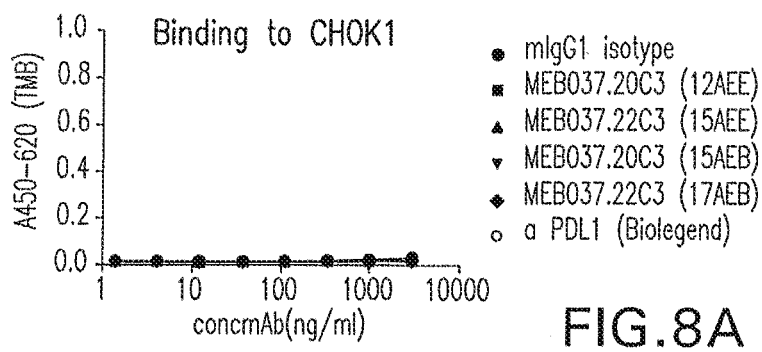
FIG. 8 illustrates the selective binding and relative affinity of antibodies 22C3 and 20C3 for hPD-L1, with the graphs showing the results of a cell-based ELISA experiment in which cells that do not express hPD-L1 (FIG. 8A), express hPDL-1 (FIGS. 8B and 8C), or express human PD-L2 (FIG. 8D) were incubated with the indicated primary antibody at the indicated concentrations, and then binding of the primary antibody detected with a secondary goat, anti-human IgG antibody as described in the Examples.
Figure 8B:
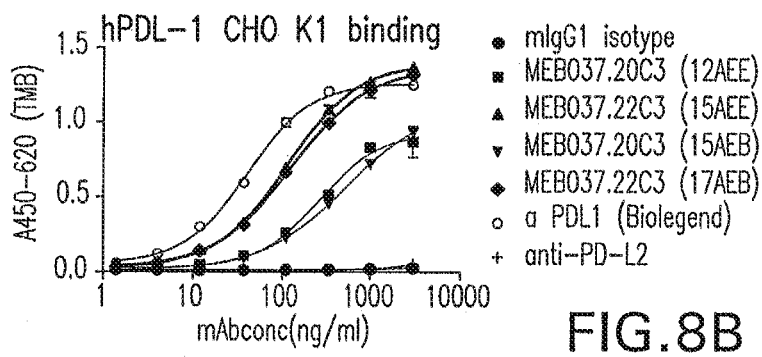
Figure 8C:
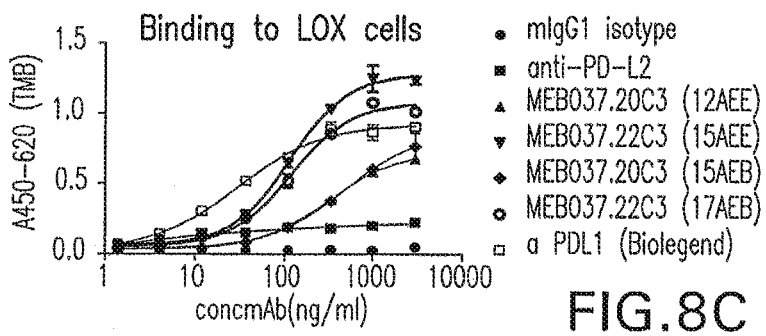
Figure 8D:
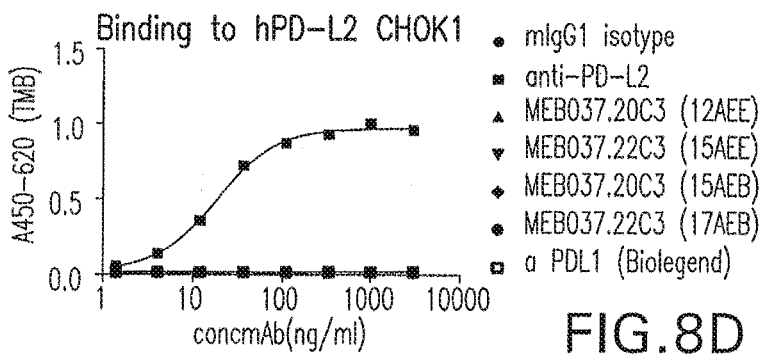

20C3 and 22C3 as well as other hPD-L1 antibodies were employed as flow cytometric reagents to detect cell surface hPD-L1. The significant right shift of both the 20C3 and 22C3 histogram curves (FIG. 6A) as compared to the isotype control antibody curve reflects selective detection of hPD-L1 on the hPD-L1-positive LOX melanoma cell line. The median fluorescent intensities associated with these histograms and others from this analysis are shown in FIG. 6B. The selectivity of 20C3 and 22C3 binding is further corroborated by the lack of significant binding (i.e. MFI of 22C3 and 20C3 comparable to isotype) on the negative cell line, HT144. In contrast, the data in FIG. 6B show that both 20C3 and 22C3 produce at least a 10-fold increase in MFI compared to isotype on the hPD-L1 positive LOX melanoma cell line. Thus, both 20C3 and 22C3 (in addition to clones 5F9, 7C8, 13D2 and 31D3) demonstrate selective binding to hPD-L1-expressing cells by flow cytometric assessment.

Another experiment evaluated the ability of the 22C3 antibody to detect expression of hPD-L1 on engineered and human cell lines. A Chinese hamster ovary (CHO) cell lines, which are negative for hPD-L1, was transfected with an expression vector encoding human PD-L1 to create an engineered positive control cell line. As shown in FIG. 7B, immunohistochemical staining with 22C3 of formalin-fixed paraffin-embedded (FFPE) cell pellets of the parental CHO cell line (negative control) and transfected CHO cell line (positive control) demonstrates appropriate positive and negative staining.

Additional FFPE human cell line pellets (A375, HS578T and LOX melanoma) were stained with 22C3 and demonstrated a range of staining patterns and intensities, as shown in FIG. 7B. 22C3 staining was strong and uniform on the Lox melanoma cells, but only showed rare, single positive cells in the A375 and HS578T cell pellets. Similar staining was observed with the 20C3 antibody (data not shown). The hPD-L1 expression levels detected in these 3 cell lines by 22C3 in the IHC assay correlated well with PD-L1 mRNA levels in these cell lines as assessed using qPCR with ubiquitin mRNA as the baseline.

The selective binding and relative affinity of 22C3 for hPD-L1-expressing cells was evaluated in a cell-based ELISA experiment. Several cell lines (hPDL1-CHOK1 cells, parental CHOK1 cells, hPDL2-CHOK1 cells, and LOX cells) were plated on individual wells of collagen-coated 96-well plates and grown to confluency. Media was removed and replaced with fresh CHOK1 media (DMEM/F12 containing 10% BCS) containing a primary antibody at increasing concentrations of between 1.4 and 3,000 ng/ml. The following primary antibodies were used: two different production lots of each of antibody 20C3 and 22C3, with a mouse IgG1 isotype an anti-PD-L1 antibody (BioLegend), and an anti-PD-L2 antibody serving as controls. The primary antibody was incubated for 1 hr at 37° C., washed 3× with PBS/0.01% Tween 20 and the secondary antibody, goat anti-human IgG, Fc specific-HRP (Southern Biotech, Cat #1030-05) conjugate was added at 1:2000 dilution in CHOK1 media. The secondary antibody was incubated for 1 hr at 37° C. and washed 5× as above. The ELISA was developed using TMB, stopped with 0.1N phosphoric acid, and the absorbance read at 450 nm with background subtraction at 650 nm. The results, which are shown in FIG. 8, demonstrate selective binding of 22C3 and 20C3 to cells expressing hPD-L1, with the affinity of 22C3 binding affinity being greater than 20C3 for both hPD-L1 CHOK1 engineered cells and LOX cells.

A similar ELISA experiment was performed to assess if either of the 20C3 or 22C3 antibodies binds to mouse PD-L1. No significant binding of either antibody to mouse PD-L1 was observed (data not shown).

Antibody binding competition assays ("cross-blocking") between different pairs of anti-hPD-L1 antibodies identified in the experiments described in Example 1 were performed. The assays employ the ForteBio® Octet® platform, which is based on bio-layer interferometry. In brief, this technique measures binding of an initial antibody (mAb1) to the biosensor tip surface as a wavelength shift (Δλ) due to the bound antibody increasing the optical thickness (Y-axis) at the biosensor tip over time (X-axis). The tip consists of an anti-huIgG sensor upon which hPD-L1-Fc is bound. The change in optical thickness upon binding of the anti-PD-L1 antibody is reflected in the upward sloping curve beginning at the first, vertical dotted red line (see graphs in FIGS. 9A, 9B and 9C), which represents the addition of a saturating concentration of mAb1 (10 micrograms/ml) into solution. After allowing for equilibration (~1000 seconds), a second antibody is injected into the assay solution (indicated by the second, vertical red dotted line in FIGS. 9A, 9B and 9C). Binding of the second mAb2, indicated by an additional excursion of the curve, suggests that the two antibodies bind to non-overlapping epitopes, whereas little to no excursion of the curve suggests that the two antibodies bind to overlapping or identical epitopes.

Figure 9A:
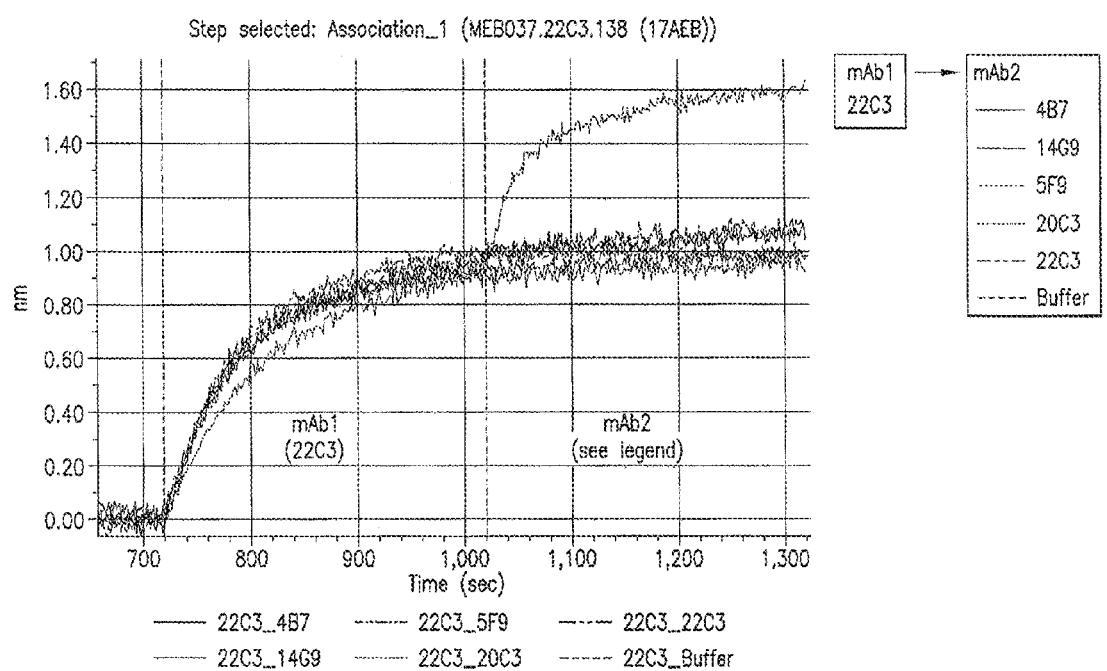
FIG. 9 shows the results of antibody binding competition assays which demonstrate that antibodies 22C3 and 20C3 bind non-identical but overlapping epitopes.
Figure 9B:
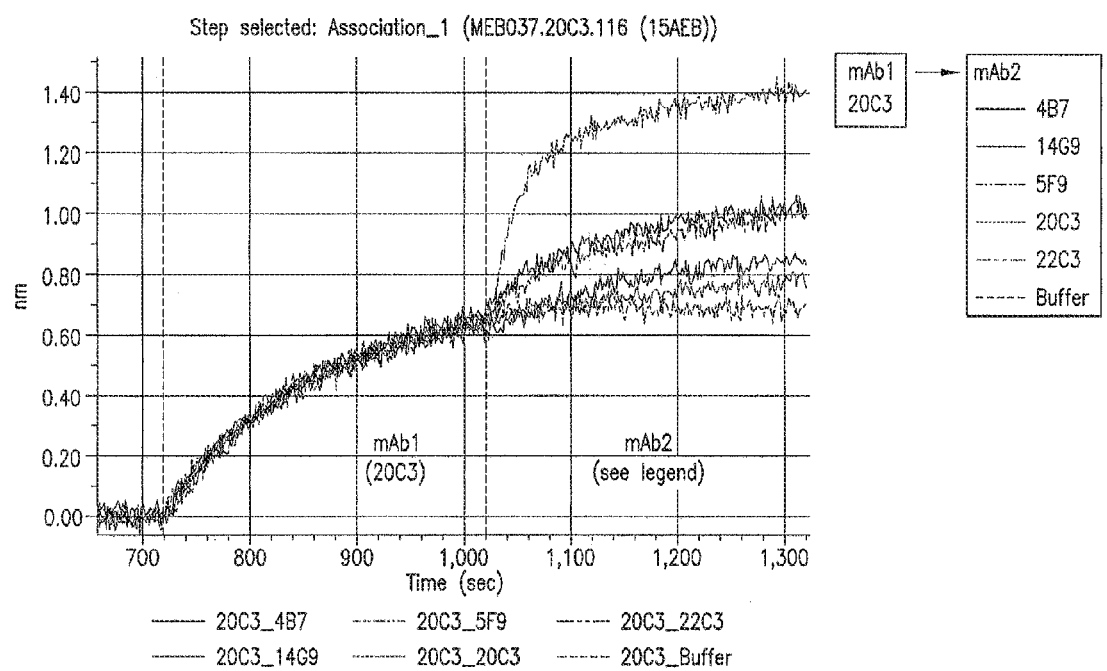
Figure 9C:
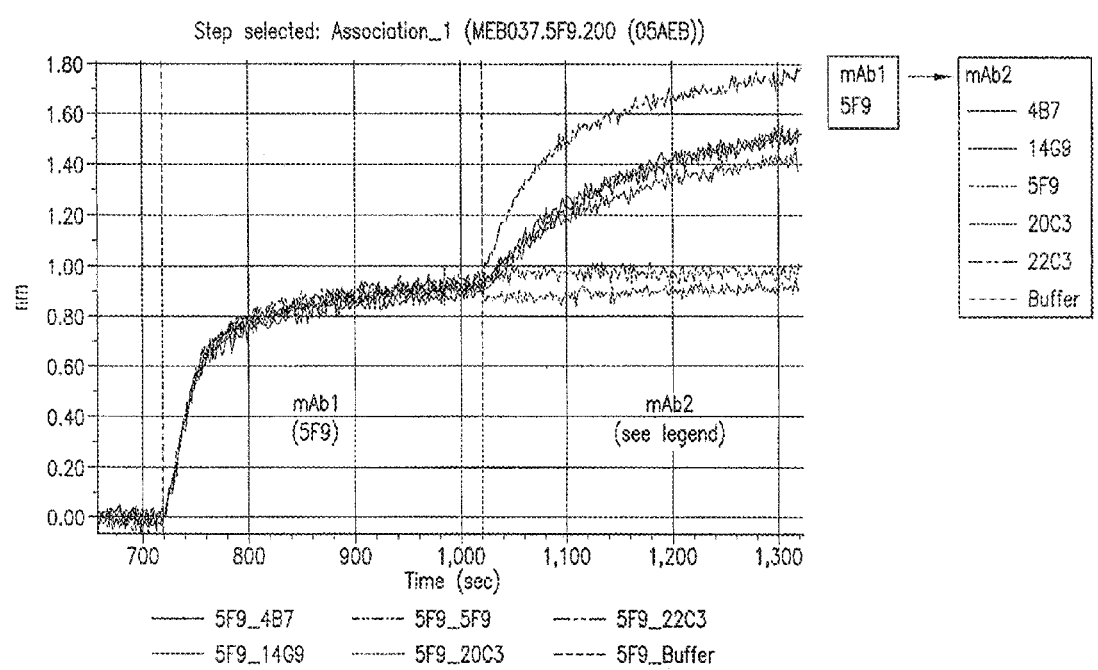

In summary, the results demonstrate that 22C3 binding competes with additional binding of all other anti-hPDL-1 clones tested as mAb2, except for 5H9 (FIG. 9A). Similarly, 20C3 also fails to compete with 5H9 binding, but shows an intermediate degree of additional binding with 22C3 as well as 4B7 (FIG. B). Taken together, these data indicate that 20C3 and 22C3 bind overlapping epitopes.

Figure 10:
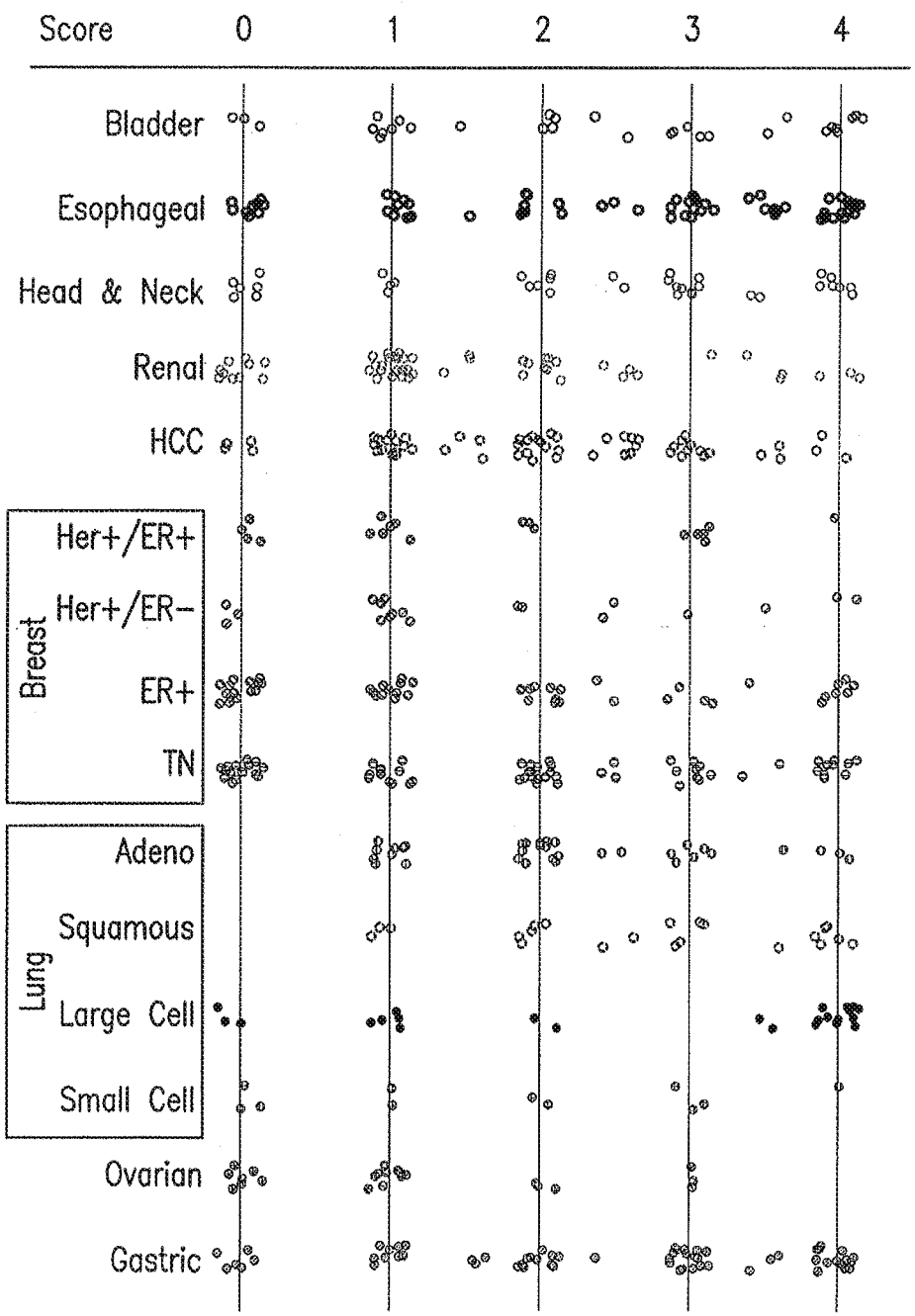
FIG. 10 illustrates the results of a semi-quantitative gestalt scoring of the intensity of 22C3 ICH staining of FFPE samples from the indicated tumor types, with the extent of staining increasing with increasing score numbers.

Ability of the 22C3 antibody to detect a range of hPD-L1 expression in different tumor types was assessed by performing IHC analysis on FFPE sections prepared from the following tumors: bladder, esophageal, head & neck, renal, HCC, breast, lung, ovarian and gastric. A preliminary screen of 22C3 reactivity with these tumor tissue sections was performed using a semi-quantitative "gestalt" interpretation of the extent of staining. As depicted in FIG. 10, 22C3 is capable of detecting a range of PD-L1 expression from essentially no staining (Score=0) to prominent, strong expression (Score=4), demonstrating the utility of IHC assay with 22C3 to guide future tumor types that may respond to interdiction of the immunosuppressive PD-1/PD-L1 interactions.

Figures 11A, 11B:
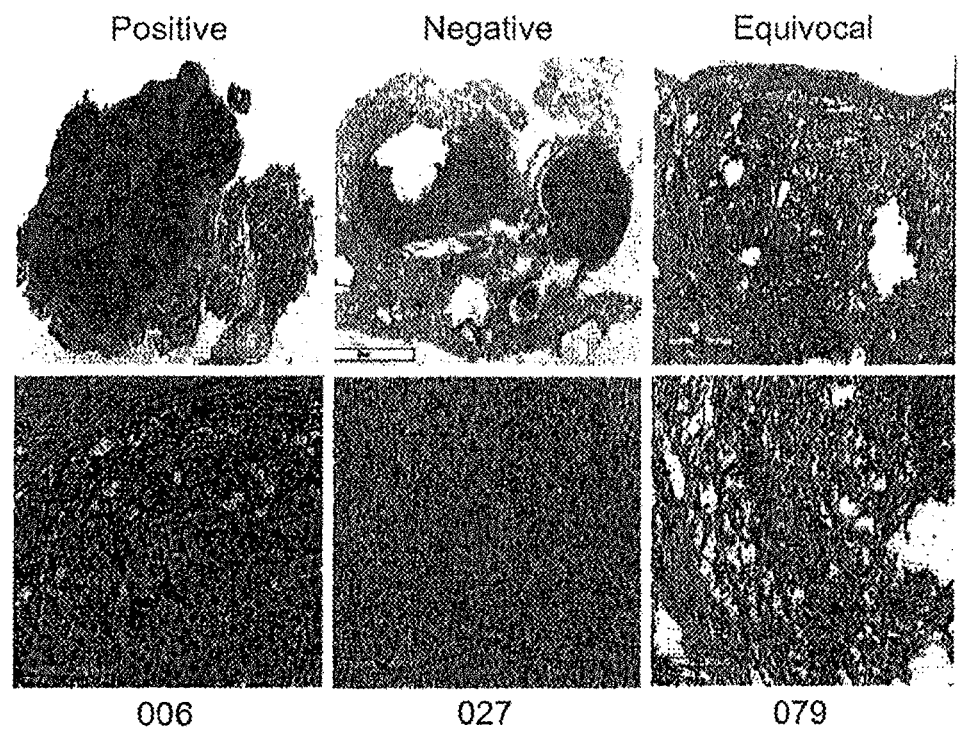
FIG. 11 illustrates that human PD-L1 expression detected with antibody 22C3 in an IHC assay correlates with response of melanoma patients to therapy with an anti-human PD-1 antibody (MK-3475), showing in FIG. 11A representative images of 22C3-IHC staining interpreted as positive, negative or equivocal for hPD-L1 expression and FIG. 11B showing the number of patients who had a positive or negative response who were scored as positive or negative (included patients scored as equivocal) for hPD-L1 expression by IHC assay.

The utility of the 22C3 antibody to stratify patients who are more likely to respond to therapy that blocks interaction of PD-1 and PD-L1, was assessed in studies were utilizing 22C3 immunohistochemical assessment of archival samples obtained from 18 melanoma patients enrolled in a phase 1 (P001) trial with MK-3475, an anti-PD1 therapeutic antibody being developed by Merck and Co., Inc. The cases were evaluated by two pathologists independently and assigned as "positive", "negative" or "equivocal", and representative images depicting these three categories are shown in FIG. 11A. Interpathologist concordance on this sample set (n=18) was 100%.

Clinical responses were assessed using immune related response criteria (irRC) and correlated with the IHC results. For this analysis, "equivocal" cases were considered to be negative, resulting in an assay sensitivity of 72% and a specificity of 86%. The results, which are shown in FIG. 11B, suggest that 22C3 immunohistochemical staining on FFPE tissue will have utility as a patient selection biomarker.

Based on the results of the experiments described above, the inventors herein determined that the antibodies produced by two of the 88 experimental hybridomas—MEB037.20C3.138 and MEB037.20C3.116—had the requisite combination of sensitivity, specificity and robustness to be considered for development as candidate FFPE-reactive IHC diagnostic reagents.

Example 3

Mapping of the Epitope on Human PD-L1 for the 22C3 Anti-PD-L1 Antibody

HDX-MS epitope mapping was performed using antibody 22C3 and a PD-L1-His protein, which contained the extracellular domain of mature human PD-L1 (SEQ ID NO:38) fused to an 11-mer histidine tag. Segments 156 to 178 and 196 to 206 on the extracellular domain of human PD-L1 (SEQ ID NO:38) showed strong protection (an average deuteration level difference of >10%) upon binding to antibody 22C3. In addition, segments 3 to 9, 10 to 13, 88 to 93, and 135 to 147 showed marginal yet significant protection (an average deuteration level difference of 5% to 10%).

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. §1.57(b)(1), to relate to each and every individual publication, database entry (e.g. Genbank sequences or GeneID entries), patent application, or patent, each of which is clearly identified in compliance with 37 C.F.R. §1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

The invention claimed is:

1. An isolated antibody or antigen binding fragment thereof that specifically binds human programmed death ligand 1 (PD-L1) as set forth in SEQ ID NO: 37 and comprises three light chain CDRs of CDRL1, CDRL2 and CDRL3 and three heavy chain CDRs of CDRH1, CDRH2 and CDRH3, wherein:
   (a) CDRL1 is selected from the group consisting of SEQ ID NO:1, SEQ ID NO:9, and SEQ ID NO:21;
   (b) CDRL2 is SEQ ID NO:2;
   (c) CDRL3 is selected from the group consisting of SEQ ID NO:3, SEQ ID NO:10, and SEQ ID NO:22;
   (d) CDRH1 is selected from the group consisting of SEQ ID NO:5, SEQ ID NO:14, SEQ ID NO:15, SEQ ID NO:26, and SEQ ID NO:27;
   (e) CDRH2 is selected from the group consisting of SEQ ID NO:6, SEQ ID NO:16, and SEQ ID NO:28; and
   (f) CDRH3 is selected from the group consisting of SEQ ID NO:7, SEQ ID NO:17, and SEQ ID NO:29.

2. The isolated antibody or antigen binding fragment thereof of claim 1, wherein the three light chain CDRs are SEQ ID NO:1, SEQ ID NO:2 and SEQ ID NO:3 and the three heavy chain CDRs are SEQ ID NO:5, SEQ ID NO:6 and SEQ ID NO:7.

3. The isolated antibody or antigen binding fragment thereof of claim 1, wherein the three light chain CDRs are SEQ ID NO:9; SEQ ID NO:2 and SEQ ID NO:10 and the three heavy chain CDRs are SEQ ID NO:14, SEQ ID NO:16 and SEQ ID NO:17.

4. The isolated antibody or antigen binding fragment thereof of claim 1, wherein the three light chain CDRs are SEQ ID NO:21, SEQ ID NO:2 and SEQ ID NO:22 and the three heavy chain CDRs are SEQ ID NO:26, SEQ ID NO:28 and SEQ ID NO:29.

5. The isolated antibody or antigen binding fragment thereof of claim 1, which comprises a light chain variable region and a heavy chain variable region, wherein:
   (a) the light chain variable region is selected from the group consisting of SEQ ID NO:4, SEQ ID NO:13, and SEQ ID NO:25; and
   (b) the heavy chain variable region is selected from the group consisting of SEQ ID NO:8, SEQ ID NO:20, and SEQ ID NO:32.

6. The isolated antibody or antigen binding fragment thereof of claim 1, which comprises a light chain variable region and a heavy chain variable region, wherein:
   (a) the light chain variable region is SEQ ID NO:13 and the heavy chain variable region is SEQ ID NO:20;
   (b) the light chain variable region is SEQ ID NO:25 and the heavy chain variable region is SEQ ID NO:32, wherein X in SEQ ID NO:32 is Q; or
   (c) the light chain variable region is SEQ ID NO:25 and the heavy chain variable region is SEQ ID NO:32, wherein X in SEQ ID NO:32 is pE.

7. The isolated antibody or antigen binding fragment thereof of claim 6 which is an IgG1 antibody.

8. An isolated antibody comprising a light chain variable region of SEQ ID NO:25, a heavy chain variable region of SEQ ID NO:32, and a mouse IgG1 constant region.

* * * * *